United States Patent
Riordan et al.

(10) Patent No.: US 9,993,585 B2
(45) Date of Patent: Jun. 12, 2018

(54) METHOD SUCTION DEVICE AND RELATED METHOD THEREOF

(71) Applicant: University of Virginia Patent Foundation, Charlottesville, VA (US)

(72) Inventors: John Philip Riordan, Charlottesville, VA (US); Bonnie V. Dougherty, Charlottesville, VA (US); Ryan M. Foley, Charlottesville, VA (US); Jessleen Kanwal, Charlottesville, VA (US); Alexander M. Guendel, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 657 days.

(21) Appl. No.: 13/672,319

(22) Filed: Nov. 8, 2012

(65) Prior Publication Data

US 2013/0131615 A1   May 23, 2013

Related U.S. Application Data

(60) Provisional application No. 61/558,606, filed on Nov. 11, 2011.

(51) Int. Cl.
*A61M 1/00* (2006.01)
*A61M 25/00* (2006.01)
*A61B 10/02* (2006.01)

(52) U.S. Cl.
CPC .......... *A61M 1/0039* (2013.01); *A61M 1/008* (2013.01); *A61B 10/0266* (2013.01); *A61M 25/0082* (2013.01); *A61M 2025/0019* (2013.01); *A61M 2025/0079* (2013.01); *A61M 2210/1028* (2013.01)

(58) Field of Classification Search
CPC ............... A61M 1/0039; A61M 1/008; A61M 2210/1028; A61M 2210/1025; A61M 2202/04; A61M 2202/06; A61M 1/0064; A61M 25/0082; A61B 17/320068; A61B 2017/320076; A61B 17/320016; A61B 17/32002; A61B 2017/32008; A61B 2017/32004; A61C 17/043; A61C 17/0202; Y10S 604/902
See application file for complete search history.

(56) References Cited

U.S. PATENT DOCUMENTS 1,485,298 A  *  2/1924  Schroyer ................. 27/24.1
3,469,582 A      9/1969  Jackson
3,958,573 A  *  5/1976  Wiley ................. A61C 17/04
                                           604/267

(Continued)

FOREIGN PATENT DOCUMENTS

EP          0 906 130          6/2005

*Primary Examiner* — Adam Marcetich
(74) *Attorney, Agent, or Firm* — Robert J. Decker

(57) ABSTRACT

A system or device for providing medical suction, particularly for intubating patients, wherein the system or device helps prevent clogging from solids dispersed in the liquid to be suctioned. This device will allow the user to effectively clear an airway or other region of the patient while minimizing the occurrence of clogs and providing for the effective and expedited unclogging of the device without the necessity of removing the device from the patient or requiring two hands to unclog.

58 Claims, 17 Drawing Sheets

(56) References Cited

U.S. PATENT DOCUMENTS

| | | | | |
|---|---|---|---|---|
| 4,136,695 A * | 1/1979 | Dafoe | A61F 6/225 | |
| | | | 128/831 | |
| 4,204,328 A * | 5/1980 | Kutner | A61C 17/043 | |
| | | | 15/418 | |
| 4,311,143 A * | 1/1982 | Komiya | A61B 18/1442 | |
| | | | 606/47 | |
| 4,445,517 A * | 5/1984 | Feild | 600/565 | |
| 4,651,752 A * | 3/1987 | Fuerst | A61B 10/0266 | |
| | | | 600/567 | |
| 4,690,672 A * | 9/1987 | Veltrup | 604/43 | |
| 4,926,877 A * | 5/1990 | Bookwalter | A61B 10/0266 | |
| | | | 600/567 | |
| 5,098,440 A * | 3/1992 | Hillstead | A61B 17/221 | |
| | | | 606/108 | |
| 5,141,503 A | 8/1992 | Sewell | | |
| 5,197,949 A | 3/1993 | Angsupanich | | |
| 5,269,768 A | 12/1993 | Cheung | | |
| 5,390,663 A * | 2/1995 | Schaefer | A61B 1/227 | |
| | | | 600/200 | |
| 5,409,013 A * | 4/1995 | Clement | 600/566 | |
| 5,486,185 A * | 1/1996 | Freitas | A61B 17/2909 | |
| | | | 606/142 | |
| 5,569,178 A * | 10/1996 | Henley | 604/22 | |
| 5,707,362 A * | 1/1998 | Yoon | A61B 17/3417 | |
| | | | 604/164.03 | |
| 5,718,677 A * | 2/1998 | Capetan et al. | 604/35 | |
| 5,776,156 A * | 7/1998 | Shikhman | A61B 17/320016 | |
| | | | 606/167 | |
| 5,823,971 A * | 10/1998 | Robinson | A61B 10/0266 | |
| | | | 600/567 | |
| 5,916,150 A * | 6/1999 | Sillman | A61B 1/227 | |
| | | | 600/184 | |
| 5,921,970 A * | 7/1999 | Vandenberg | 604/264 | |
| 5,972,013 A * | 10/1999 | Schmidt | 606/185 | |
| 6,136,014 A * | 10/2000 | Sirimanne | A61B 10/0266 | |
| | | | 606/170 | |
| 6,293,945 B1 * | 9/2001 | Parins | A61B 18/1402 | |
| | | | 606/45 | |
| 6,390,975 B1 * | 5/2002 | Walls | A61B 1/32 | |
| | | | 600/200 | |
| 6,656,197 B1 * | 12/2003 | LaHaye | A61F 9/00802 | |
| | | | 604/289 | |
| 7,244,250 B2 | 7/2007 | Miki | | |
| 7,625,207 B2 | 12/2009 | Hershey | | |
| 7,802,574 B2 | 9/2010 | Schultz | | |
| 8,172,857 B2 | 5/2012 | Fogel | | |
| 8,251,945 B2 | 8/2012 | Secrest | | |
| 8,262,645 B2 | 9/2012 | Bagwell | | |
| 8,292,909 B1 | 10/2012 | Dubois | | |
| 8,298,254 B2 | 10/2012 | Dubois | | |
| 2002/0108614 A1 | 8/2002 | Schultz | | |
| 2005/0137453 A1 * | 6/2005 | Ouchi | A61B 1/00087 | |
| | | | 600/106 | |
| 2005/0165345 A1 * | 7/2005 | Laufer et al. | 604/26 | |
| 2005/0240165 A1 | 10/2005 | Miki | | |
| 2005/0279359 A1 | 12/2005 | LeBlanc | | |
| 2006/0025720 A1 * | 2/2006 | Sawa | A61M 25/0084 | |
| | | | 604/164.01 | |
| 2006/0224082 A1 * | 10/2006 | Vetter et al. | 600/564 | |
| 2009/0125036 A1 * | 5/2009 | Bleich | 606/110 | |
| 2010/0081875 A1 * | 4/2010 | Fowler | A61B 1/00149 | |
| | | | 600/114 | |
| 2010/0154799 A1 | 6/2010 | Brewer | | |
| 2011/0028939 A1 * | 2/2011 | Yarger | 604/523 | |
| 2011/0034775 A1 * | 2/2011 | Lozman | A61B 17/1684 | |
| | | | 600/204 | |
| 2011/0105838 A1 | 5/2011 | Fogel | | |
| 2012/0227207 A1 | 9/2012 | Berry | | |
| 2013/0023818 A1 * | 1/2013 | Rosenblum | A61F 11/002 | |
| | | | 604/28 | |
| 2013/0053828 A1 * | 2/2013 | Hensler et al. | 604/541 | |

* cited by examiner

FIG. 1A

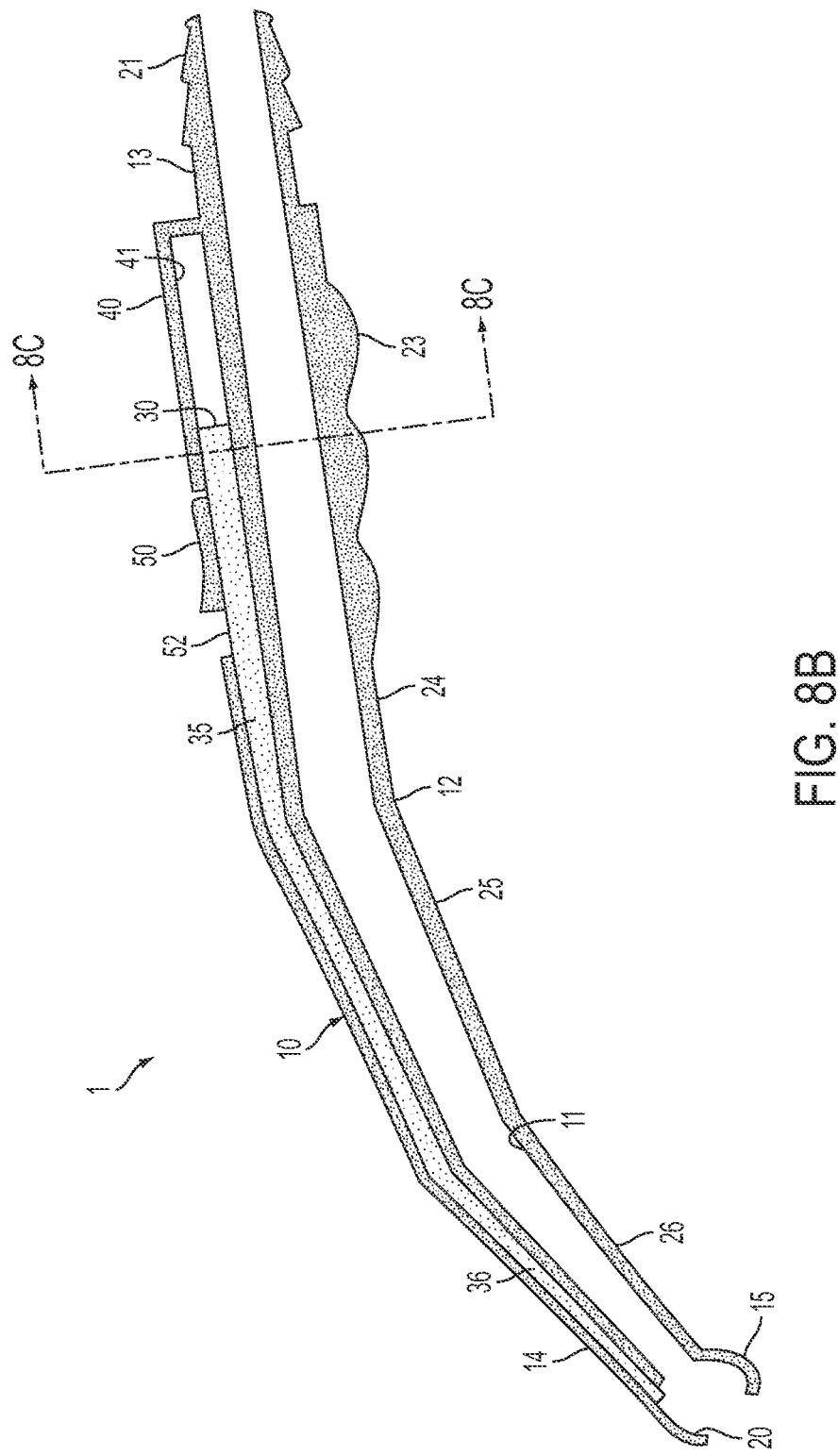

METHOD SUCTION DEVICE AND RELATED METHOD THEREOF

CROSS REFERENCE TO RELATED APPLICATIONS

The present application claims priority under 35 U.S.C. § 119(e) from U.S. Provisional Application Ser. No. 61/558,606, filed Nov. 11, 2011, entitled "Medical Suction Device and Related Method;" the disclosure of which is hereby incorporated by reference herein in its entirety.

FIELD OF THE INVENTION

The present invention relates generally to the field of medical devices to be used for medical or veterinary suctioning procedures. More specifically, the invention is in the subfield of intubation and clearing debris and liquid or other material from regions within the patient.

BACKGROUND OF THE INVENTION

Annually, 123.8 million patients will visit the Emergency Department (ED), of which an estimated 8 million will require the use of a suction device. Current suction devices used in the ED are deficient in providing continuous suction power and clear visibility while establishing a clear airway for a patient and allowing intubation. The most widely used suction device, the Yankauer suction tip, clogs frequently and must be removed from the patient in order to unclog and re-establish suction. Removing the tip from the field results in distractions, delayed clearing of liquids and debris from the patient, and loss of concentration by the physician during critical moments of intubation. Therefore, an area for significant improvement in design exists.

The ability to visualize important anatomical structures is imperative to perform medical evaluation and treatment. Too often, this process is complicated by the obstruction of the suction device by solids and liquids.

Moreover, current suction devices that are used in the medical field are limited by obstruction of the lumen and subsequent loss of function. Once this occurs, the practitioner must remove the device and manually remove the debris, often requiring both hands or replacement of the device with a new one. This process takes time and is inefficient.

Therefore, there is a need in the art for an improved medical suction device. Particular needs remain to allow physicians and medical workers to remove liquids, solids, and other materials from the patient while reducing the incidence of obstruction of the suction device, and allowing the user to unclog the device easily and quickly without interrupting the procedure.

SUMMARY OF THE INVENTION

An aspect of an embodiment of the present invention provides a medical suction device (aka "Gator") and related method that is used to suction body fluids such as blood and vomit. An aspect of an embodiment of the present invention provides a medical suction device and related method that provides a unique mechanism that, among other things, facilitates clearance of obstructing solids such as blood clots and food particles. The present invention device and method improves the usability of the hand held suction device.

An aspect of an embodiment will provide improved clearance of these substances, thus, allowing the practitioner better circumstances for performing medical procedures. This will improve efficiency and reduce complications.

An aspect of an embodiment of the present invention is to allow the device to provide continuous suction power without clogging while also providing a specific protocol for unclogging. The device will facilitate the removal of obstructions from the aperture of the suction lumen with single-handed operation and while remaining in communication with the region of the patient to be cleared.

An aspect of an embodiment of the present invention provides, among other things, a medical suction device for use on a subject, wherein the device is to be used with a vacuum source for the purpose of transferring material from a region of the subject to a collection area. The device may comprise: a lumen having an inner wall and an outer wall, the lumen having a distal end and a proximal end, the proximal end being in communication with the vacuum source, the distal end including an aperture, wherein the lumen is configured to be used in the region of the subject; an elongated interacting member substantially aligned with the lumen, the elongated interacting member having a distal end and a proximal end; and an actuator in communication with the elongated interacting member, wherein the actuator is configured to drive the distal end of the elongated interacting member through the aperture or adjacent to the aperture to interact with the material to assist the material transfer by mitigating or preventing obstruction in the aperture or the lumen by the material, while the lumen is configured to remain in communication with the vacuum source and remain in the region of the subject.

An aspect of an embodiment of the present invention provides, among other things, a medical suction device for use on a subject for the purpose of transferring material from a region of the subject to a collection area, wherein the device is to be used with a) a lumen and b) a vacuum source; and whereby the lumen may have an inner wall and an outer wall, the lumen have a distal end and a proximal end, the proximal end being in communication with the vacuum source, the distal end including an aperture, wherein the lumen is configured to be used in the region of the subject. The device may comprise: an elongated interacting member substantially aligned with the lumen, the elongated interacting member having a distal end and a proximal end; and an actuator in communication with the elongated interacting member, wherein the actuator is configured to drive the distal end of the elongated interacting member through the aperture or adjacent to the aperture to interact with the material to assist the material transfer by mitigating or preventing obstruction in the aperture or the lumen by the material, while the lumen is configured to remain in communication with the vacuum source and remain in the region of the subject.

An aspect of an embodiment of the present invention provides, among other things, a method of using medical suction on a subject, wherein the medical suction is provided by a vacuum source, wherein the method is for the purpose of transferring material from a region of the subject to a collection area. The method may comprise: inserting a lumen in the region of the subject; providing an elongated interacting member substantially aligned with the lumen, the elongated interacting member having a distal end and a proximal end; and driving an actuator in communication with the elongated interacting member to drive the distal end of the elongated interacting member through the lumen or adjacent to lumen to interact with the material to assist the material transfer by mitigating or preventing obstruction in the lumen by the material, as the lumen continues to remain in communication with the vacuum source and remain in the region of the subject.

These and other advantages and features of the invention disclosed herein, will be made more apparent from the description, drawings and claims that follow.

DESCRIPTION OF THE DRAWINGS

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

FIGS. 1(A) and 1(B) provide schematic illustrations of an elevation sectional view of an embodiment of the suction device in its retracted and deployed positions, respectively.

FIGS. 2(A) and 2(B) also illustrate the elongated interacting member with a protrusion member on the distal end, displaying both a proximal and distal surface. This protrusion member may be, but is not limited to, any one of the protrusions on the elongated interacting member called out in either the specification or claims.

FIG. 8(B) provides a schematic elevation view of the embodiment of the medical suction device shown in FIG. 8(A).

DETAILED DESCRIPTION OF EXEMPLARY EMBODIMENTS OF THE INVENTION

Figure 1A:
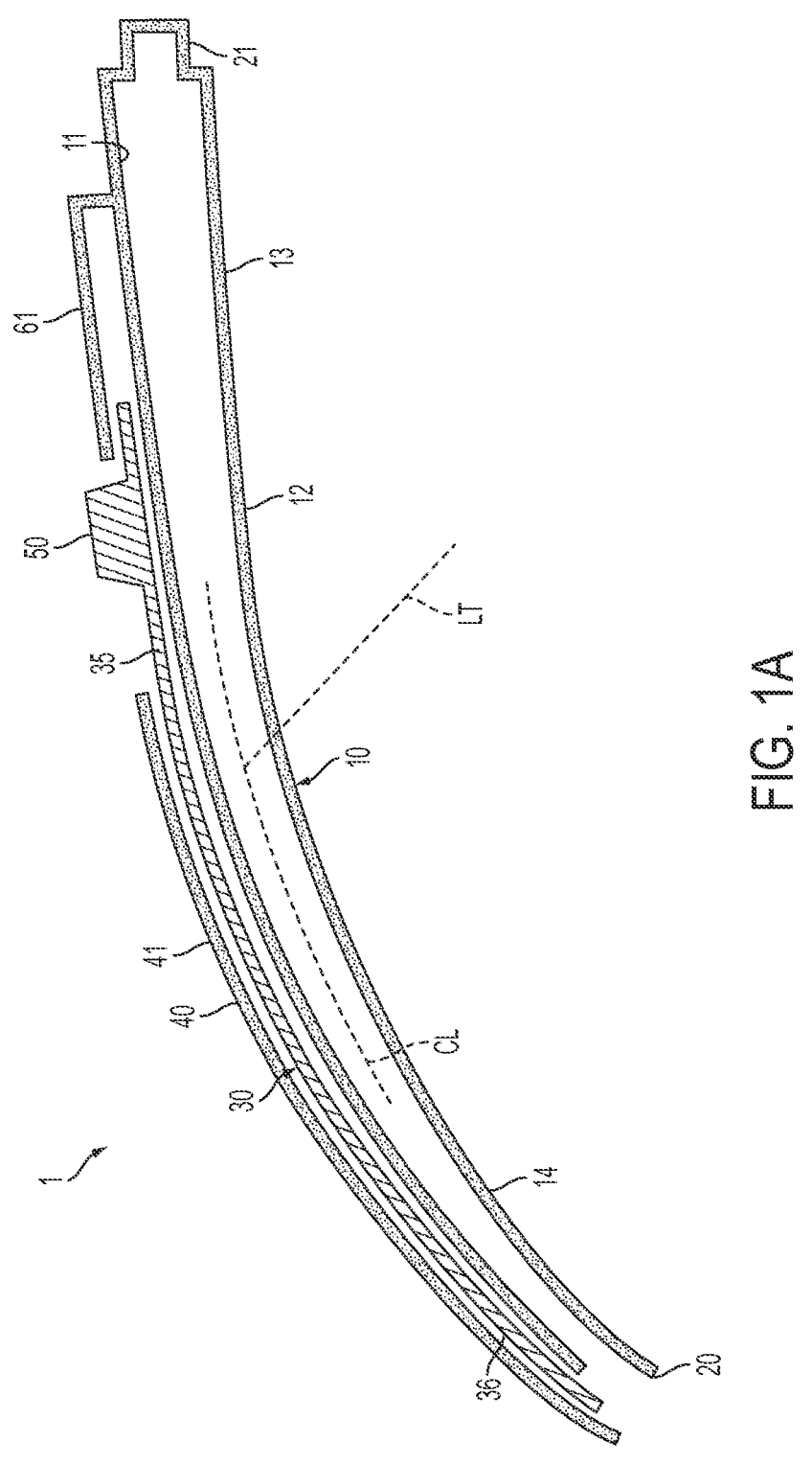
Figure 1B:
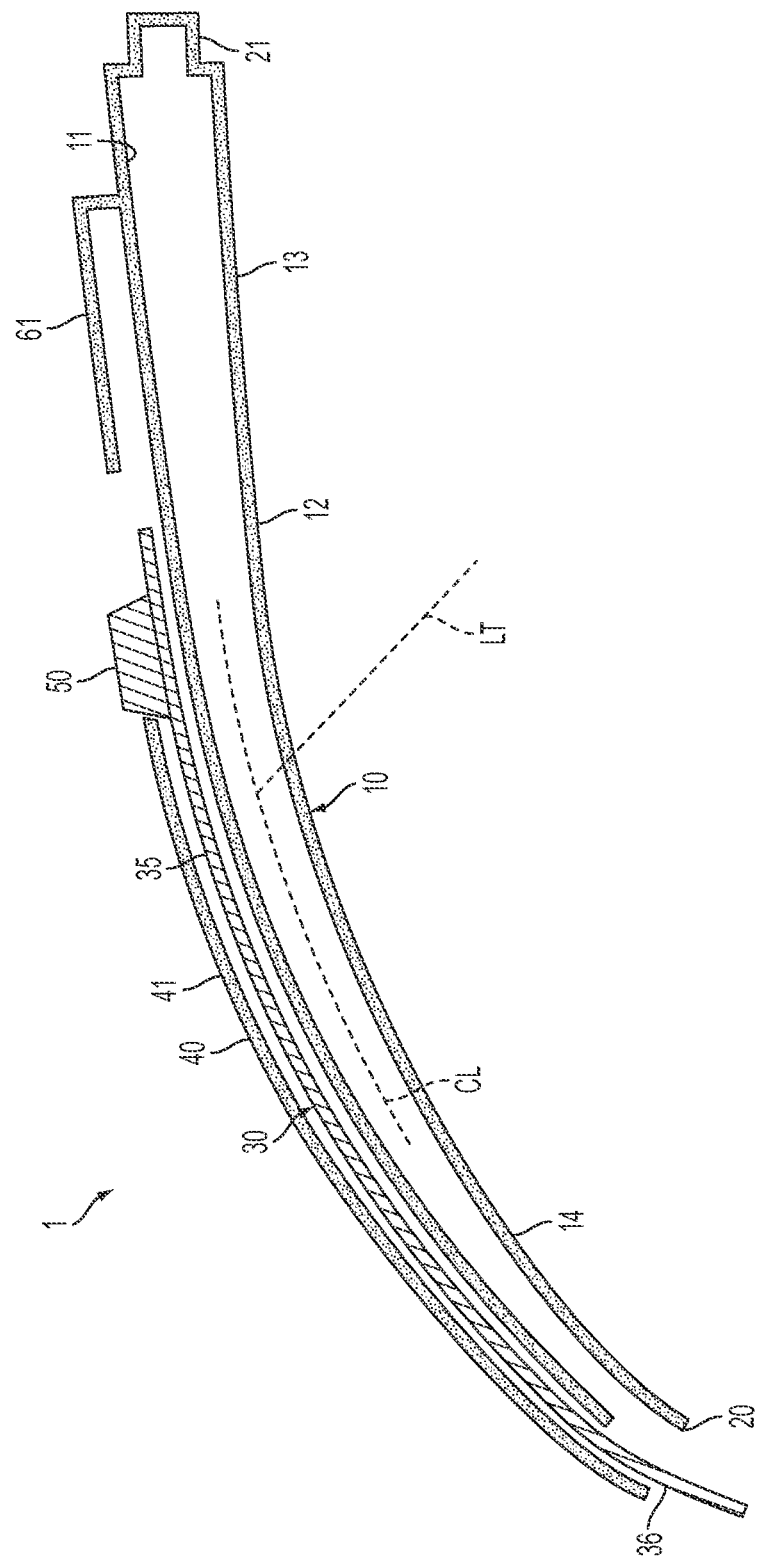

FIGS. 1(A)-(B) provides a schematic illustration of an elevation sectional view of an embodiment of the present invention medical suction device 1 for use on a subject (not shown) that may be used with a vacuum source (not shown) for the purpose of transferring material from a region of the subject to a collection area. An embodiment of the present invention device 1 may include a lumen 10 having an inner wall 11 and an outer wall 12. The lumen 10 has a distal end 14 and a proximal end 13, and the proximal end 13 may be configured to be in communication with a vacuum source (not show). For instance, the device 1 may have some sort of port 21 to connect to a hose or tube that is in communication with the vacuum supply. The distal end 14 may include an aperture 20 whereby the lumen 10 is configured to be used in the region of the subject. The device 1 may also include an elongated interacting member 30 that may be substantially aligned with the lumen 10. The elongated interacting member 30 includes a distal end 36 and a proximal end 35. FIG. 1(A) illustrates the elongated interacting member 30 in a retracted position. Although in the instant illustration of FIGS. 1(A)-(B), the elongated interacting member 30 is shown outside of the inner wall 11 of the lumen 10, as will be discussed in this disclosure, the location and operation of the elongated interacting member 30 may vary. The device 1 may also include an actuator 50 in communication with the elongated interacting member 30. The actuator 50 is configured to drive the distal end 36 of the elongated interacting member 30 through the aperture 20 or adjacent to the aperture 20 to interact with the material to assist the material transfer by mitigating or preventing obstruction of the aperture 20 or lumen 10 by the material while the lumen 10 remains in communication with the vacuum source and in the region of the subject. Still referring to FIGS. 1(A)-(B), the elongated interaction member may be disposed within or by a retention member 40. For example, as shown the retention member 40 is an elongated hollow chamber 41.

Still referring to FIGS. 1(A)-(B), the device 1 may be operated whereby the device can simply be hand held by the user, wherein the actuator is controlled by the user during the transferring of the material while the device is in the region of the subject. The device does not require removal from the region of interest of the subject, nor does it require more than one hand to operate. The device 1 may be implemented with the actuator 50 that comprises a pad or grip to be configured for contact by any digit of the user.

Referring to FIG. 1(B), the device 1 is shown in its deployed position. For instance, in an embodiment the deployed position is achieved by the actuator 50 driving distal end 36 of the elongated interacting member 30, moving the elongated interacting member distally to provide the assistance so as to push the material present in the aperture 20 or adjacent to the aperture 20 so as to disrupt the material in the aperture 20 or lumen 10.

Thereafter, the device may return to or partially return to its retracted position by the actuator 50 driving distal end 36 of the elongated interacting member 30 proximally to provide the assistance so as to pull the material present in the aperture 20 or adjacent to the aperture 20 so as to disrupt the material in the aperture 20 or lumen 10.

It should be appreciated that the elongated interacting member 30 may move back and forth between the deployed and retracted positions any number of times, as well as any interim positions there between.

Figure 2A:
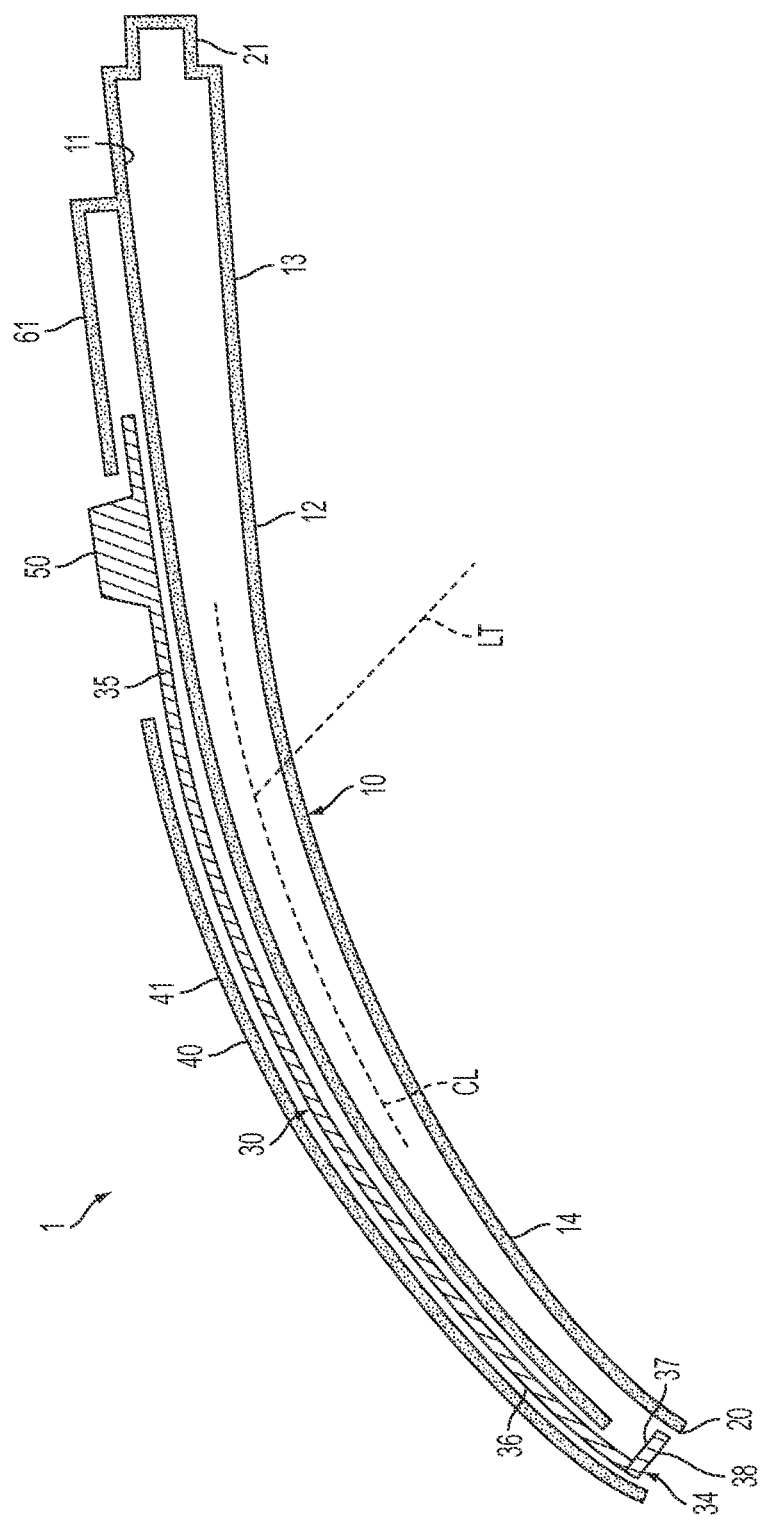
FIGS. 2(A) and 2(B) provide schematic illustrations of an elevation sectional view of an embodiment of the suction device in its retracted and deployed positions, respectively.
Figure 2B:
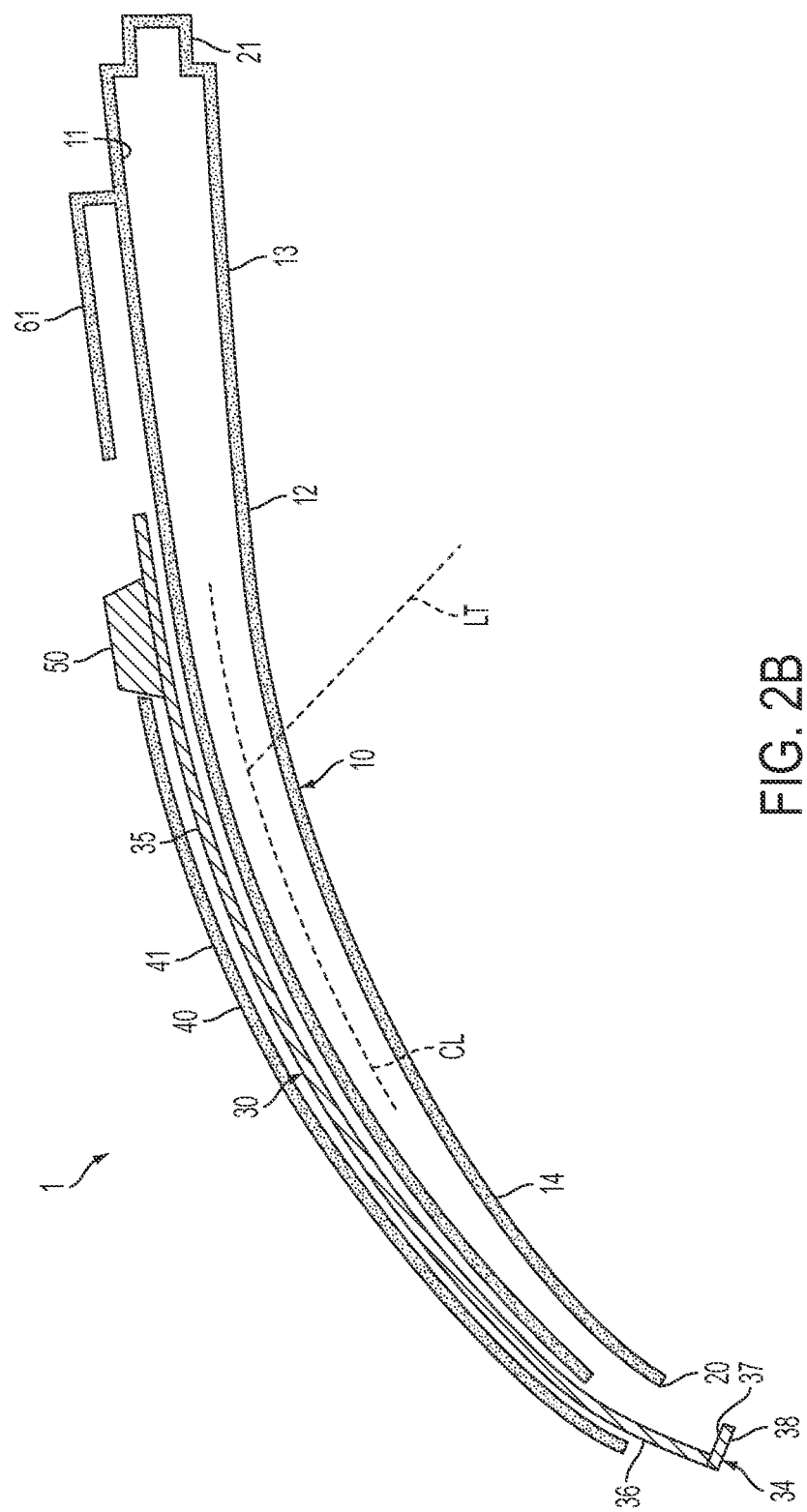

FIGS. 2(A)-(B) provide an embodiment of the present invention medical suction device 1 similar to that of FIG. 1, but with a protrusion member 34 disposed on the distal end 36 of said elongated interacting member 30. As such, the driving of said distal end of said elongated interacting member may include moving said elongated interacting member proximally to provide the assistance so as to deform the material present in said aperture or adjacent to said aperture so as to disrupt the material in said aperture or said lumen. It should be appreciated that the elongated interacting member 30 may move back and forth between the deployed and retracted positions any number of times, as well as any interim positions there between.

Referring to FIGS. 1 and 2, for purpose of illustration the lumen may be presented relative to a centerline (CL). The lumen 10 may have a variety of alignments and curvatures as desired or required. For instance the lumen 10 may be substantially straight thereby having a centerline (CL) that is substantially straight. The lumen 10 may also be curved thereby having a centerline (CL) that is curved. The lumen 10 also may be curved so as to have curvature along the centerline (CL) having a variable radius. The device 1 may have a lumen 10 that has multiple segments aligned along said centerline (CL) wherein one or more adjacent segments are angled longitudinally or laterally from one another, or any combination thereof. The lumen 10 may also have a variety of cross sectional (as taken with respect to the centerline (CL)) shapes including, but not limited to, circular, ovoid, elliptical, or any other polygonal, regular, or irregular shape that may be useful in practice. It is also contemplated that the lumen 10 may have geometric features along its inner wall 11. Such features may include, but are not limited to, groves or ridges that engage the elongated interacting member 30 in order to direct it down a particular trajectory through the lumen 10 or retention member 40. These interior features may also be used to aid flow or reduce the chances of obstruction throughout the lumen 10 itself. Longitudinal is defined as being in the plane of the paper and laterally is defined as being normal (90 degrees) with the paper (as illustrated by "LT").

Referring to FIGS. 2(A)-(B), the protrusion member 34 may have a proximal surface 37 and distal surface 38. In an approach, for example, the proximal surface 37 of the protrusion member may be configured as a cutting edge or with a cutting edge attached thereto. As such the driving of said distal end 36 of said elongated interacting member 30 includes moving said elongated interacting member proximally to provide the assistance so as to cut the material present in said aperture 20 or adjacent to said aperture 20 so as to disrupt the material in said aperture 20 or said lumen 10. It should be appreciated that the elongated interacting member 30 may move back and forth between the deployed and retracted positions any number of times, as well as any interim positions there between. It should further be appreciated that there may be more than one protrusion 34 having a variety of sizes, materials, dimensions, contours and functions as desired or required. Further, the cutting edge may be provided on the distal surface 38 of the protrusion 34, or on both the protrusion distal surface 38 and protrusion proximal surface 37. It should be appreciated that any surface associated with the protrusion may be sharpened or contoured as desired or required.

Similarly, it should be appreciated that one or more portions of said elongated interacting member 30 can be disposed outside the lumen 10, and one or more portions of said elongated interacting member 30 are disposed inside said lumen 10. Still yet, it should be appreciated that one or more portions of said elongated interacting member 30 may be disposed a) within the retention member 40 b) inside the lumen 10 and c) outside the lumen 10, or in any combination thereof.

It should be appreciated that the elongated interacting member 30, lumen 10, and/or actuator 50 may be manufactured, sold, or shipped separately, as well as any combination thereof. Similarly, it should be appreciated that the elongated interacting member 30, lumen 10, actuator 50 and/or a vacuum supply (as well as vacuum port) may be manufactured, provided, sold, or shipped separately. A vacuum supply may be remote or local and attachable and/or detachable in various approaches.

Still referring to FIGS. 2(A)-(B), the device 1 may include one or more protrusions 34 that are pivotally attached or disposed in communication with the distal end 36 of the elongated interacting member 30. An aspect of an embodiment of the present invention device includes the one or more protrusions 34 that may be comprised of a variety of materials and structural designs. For instance, one or more protrusions 34 may be comprised of a flexible material, rigid material, or various portions that each may have flexible materials or rigid materials. For the purposes of this device, a flexible material is one that has a modulus of elasticity such that it will appreciably deform or deflect during the normal use of the device to enhance function. A rigid material is one that has a modulus of elasticity such that it will not appreciably deform during the normal use and function of the device. For instance, the one or more protrusions 34 may be comprised of a flexible structural design/structures, rigid structural design/structures, or various portions that each may have both flexible structural designs/structures and rigid structural designs/structures.

An aspect of an embodiment of the present invention device includes the one or more protrusions 34 that may be comprised of a variety of materials and structural designs. For instance, cutting edges (or bending edges) of the one or more protrusions 34 may be comprised of a flexible material, rigid material, or various portions that each may have flexible materials or rigid materials. For instance, the cutting edges (or bending edges) of one or more protrusions 34 may be comprised of a flexible structural design/structures, rigid structural design/structures, or various portions that each may have both flexible structural designs/structures and rigid structural designs/structures. Similarly, the cutting edges (bending edges) may be proximally curved, distally curved, or a combination of proximal and distal-shaped curves (as well as any laterally directed curves).

It should be appreciated that the one or more protrusions 34 may be a brush or any variety of tools or structures as desired or required.

An aspect of an embodiment of the present invention device 1 includes the elongated interacting member 30 to be comprised of a variety of materials and structural designs. For instance, the elongated interacting member 30 may be comprised of a flexible material, rigid material, or various portions that each may have flexible materials or rigid materials. For instance, the elongated interacting member 30 may be comprised of a) flexible structural design/structures, b) rigid structural design/structures, c) various portions that each may have both flexible structural designs/structures and rigid structural designs/structures or d) various portions that each may have blended flexible and rigid designs/structures.

Next, as will be discussed in greater detail in this disclosure, it should be appreciated that the elongated interacting member 30 may be disposed inside the lumen 10, outside the lumen 10, a combination of both outside and inside the lumen 10, or in a retention member 40 such as: a) a separate chamber; b) hooks, brackets, or mounts; or c) a combination of a chamber along with either hooks, brackets or mounts.

Figure 3:
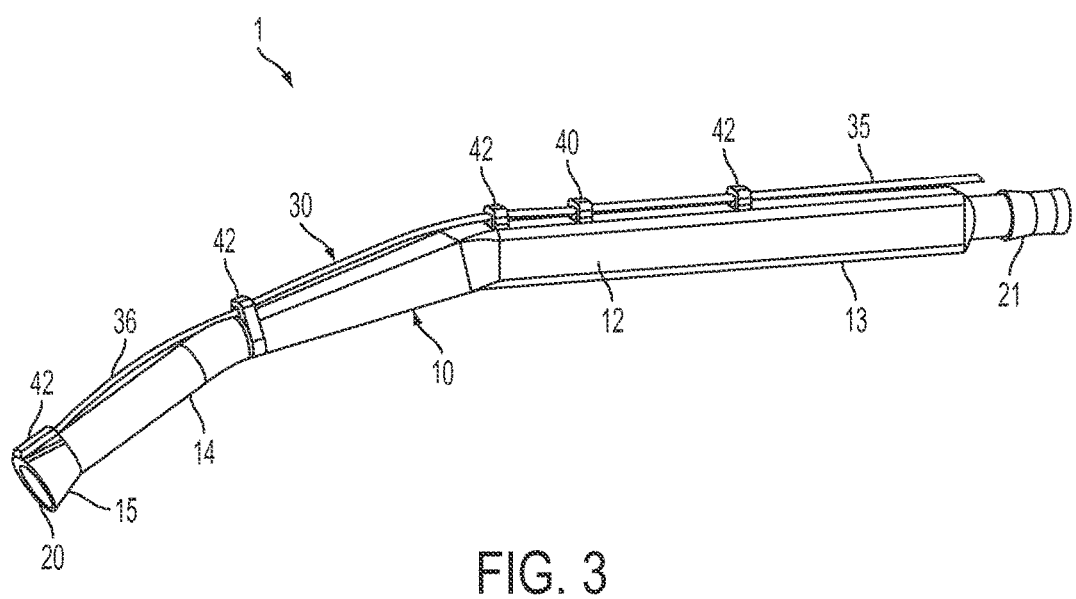
FIG. 3 provides a schematic illustration of a perspective view of an embodiment of the present invention medical suction device.

FIG. 3 provides a schematic illustration of a perspective view of an embodiment of the present invention medical suction device 1 for use on a subject (not shown) that may be used with a vacuum source (not shown) for the purpose of transferring material from a region of the subject to a collection area. An embodiment of the present invention device 1 may include a lumen 10 having an outer wall 12. The lumen 10 has a distal end 14 and a proximal end 13, and the proximal end 13 may be configured to be in communication with the vacuum source (not show). For instance, the device 1 may have some sort of port 21 to connect to a hose or tube that is in communication with the vacuum supply. The distal end 14 may include an aperture 20 at the distal tip 15 of the lumen 10 whereby the lumen 10 is configured to be used in the region of the subject. The device 1 may also include an elongated interacting member 30 that may be substantially aligned with the lumen 10. The elongated interacting member 30 includes a distal end 36 and a proximal end 35. FIG. 3 illustrates the elongated interacting member 30 in a retracted position. The instant illustration of FIG. 3 sets forth the elongated interacting member 30 shown outside of the outer wall 12 of the lumen 10, and retained by the retention member 40, which in this instance is a set of bracket or hooks 42. The device 1 may also include an actuator 50 (not shown) in communication with the elongated interacting member 30. The actuator 50 (not shown) is configured to drive the distal end 36 of the elongated interacting member 30 adjacent to the aperture 20 to interact with the material to assist the material transfer by mitigating or preventing obstruction of the aperture 20 or lumen 10 by the material while the lumen 10 remains in communication with the vacuum source and in the region of the subject.

Figure 4A:
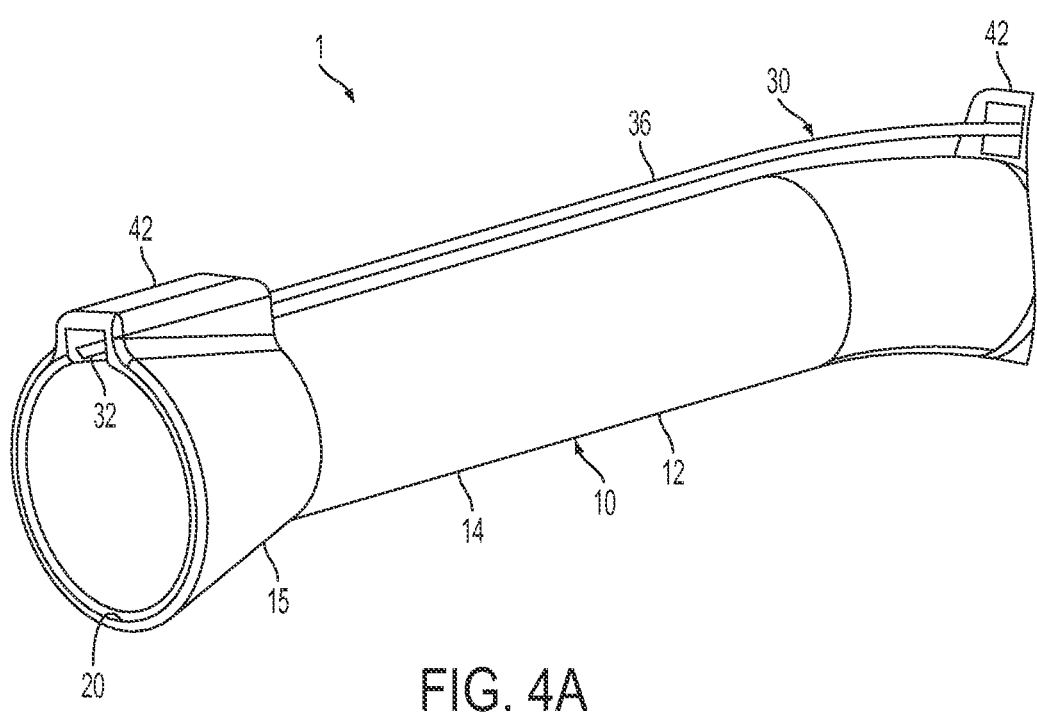
FIGS. 4(A)-(B) provides an enlarged partial view of the embodiment of the medical suction device of FIG. 3 having the elongated interacting member aligned above the outer wall of the lumen (FIG. 4(A)) and partially above the outer wall and partially below the inner wall of the lumen (FIG. 4(B)).
Figure 4B:
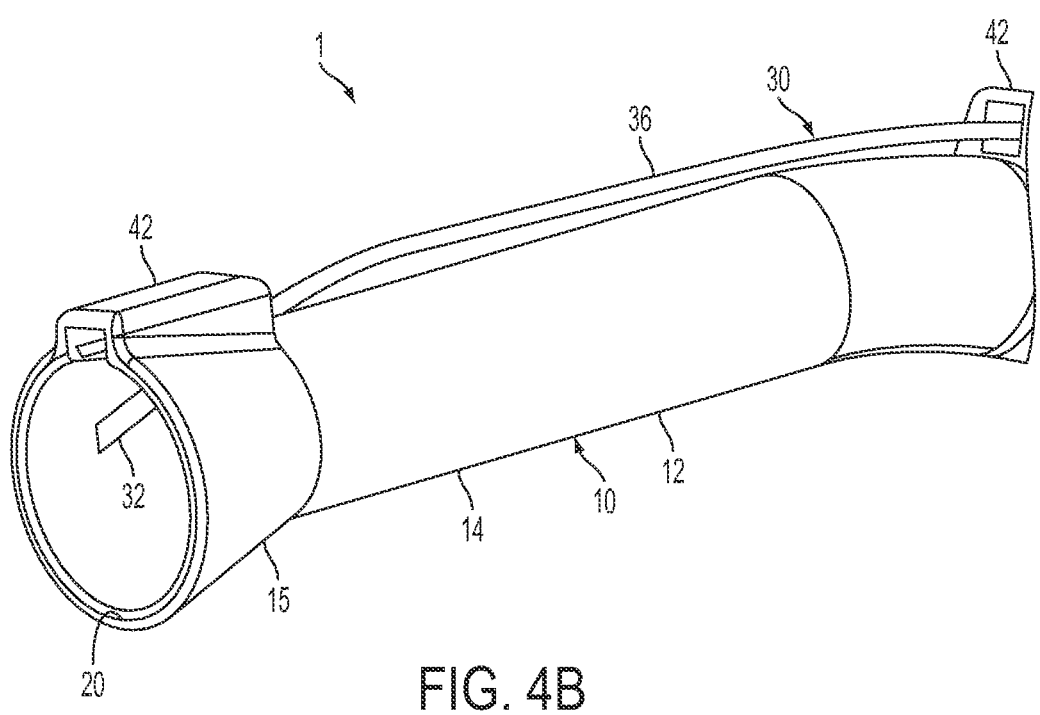

FIGS. 4(A)-(B) provides an enlarged partial view of the embodiment (at the distal end) of the medical suction device of FIG. 3. As shown FIG. 4(A), the elongated interacting member 30 is aligned above the outer wall of the lumen 12. As shown in FIG. 4(B), the elongated interacting member 30 is aligned partially above the outer wall of the lumen 12 and partially below the inner wall of the lumen 11 (FIG. 4(B)).

Figure 5A:
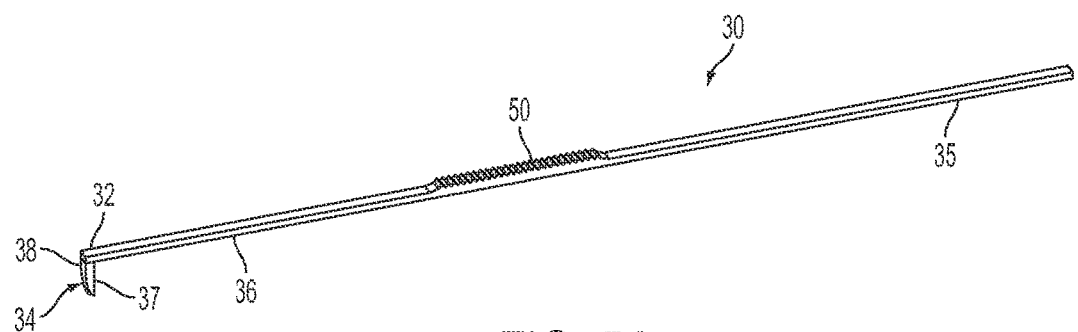
FIG. 5(A) provides a schematic illustration of a perspective view of the elongated interacting member 30 of an embodiment of the present invention medical suction device.

FIG. 5(A) provides a schematic illustration of a perspective view of the elongated interacting member 30 of an embodiment of the present invention medical suction device. The elongated interacting member 30 has a proximal end 35 and a distal end 36, as well as an actuator 50. Also, protrusion member 34 is disposed at the tip 32 of the elongated interacting member 30. The protrusion member 34 may have a proximal surface 37 and distal surface 38.

Figure 5B:
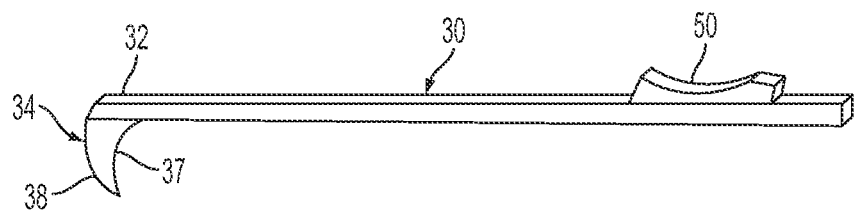
FIGS. 5(B)-(F) provide schematic illustrations of perspective views of several specific embodiments of the elongated interacting member.

FIG. 5(B) provides a schematic illustration of a perspective view of an embodiment of elongated interacting member 30 of the present invention medical suction device. In this embodiment, the elongated interacting member 30 includes a protrusion member 34 at the distal tip 32, which is shaped as in a sickle or tooth-like manner. This protrusion member 34 may be used to disrupt, dislodge, or otherwise agitate any obstructions in the distal tip of the lumen, the aperture of the lumen, or lumen. This protrusion member 34 may be made with varying degrees of sharpness to the proximal surface 37 or distal surface 38, or both the proximal surface 37 and distal surface 38. This allows the protrusion member 34 to be made in a variety of combinations to agitate, fold, disrupt, or cut any obstructions in either the proximal or distal directions.

Figure 5C:
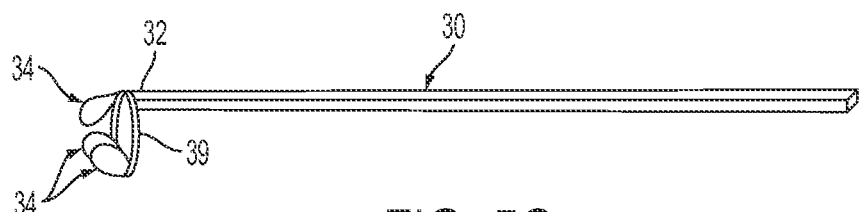

FIG. 5(C) provides a schematic illustration of a perspective view of an embodiment of elongated interacting member 30 of the present invention medical suction device. In this embodiment, the elongated interacting member 30 includes a ring-type protrusion 39 located at the distal tip 32, which itself includes protrusion members 34. This embodiment is intended to agitate obstructing particles in all areas of the tip without blocking suction. In this embodiment, each protrusion member 34 is spaced along the circumference of the ring-type protrusion 39 to engage with a wall aperture on the distal tip of the lumen when the elongated interacting member 30 is in its distal position. This allows the protrusion members 34 to obscure the wall apertures and increase suction through the distal tip of the lumen, aperture of the lumen, and/or the lumen. The additional suction, in combination with the proximal and distal motion of the elongated interacting member 30 will help to return flow through the distal tip of the lumen, lumen aperture, and the lumen.

Figure 5D:
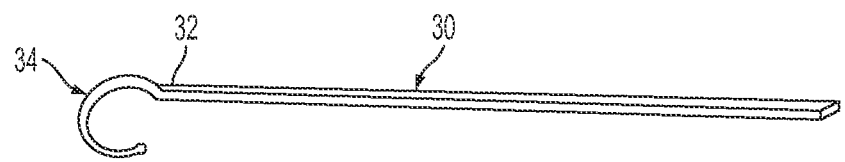

FIG. 5(D) provides a schematic illustration of a perspective view of an embodiment of elongated interacting member 30 of the present invention medical suction device. In this embodiment, the protrusion member 34 is a hook located at the distal tip 32, curved proximally to enhance its function of disrupting an obstruction in the proximal direction of the device.

Figure 5E:
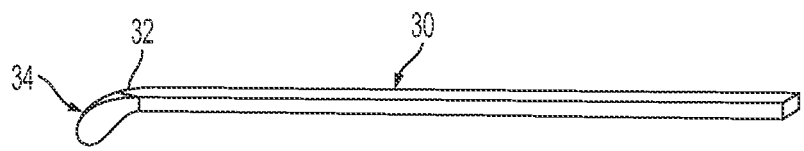

FIG. 5(E) provides a schematic illustration of a perspective view of an embodiment of elongated interacting member 30 of the present invention medical suction device. In this embodiment, the protrusion member 34 located at the distal tip 32 is a prodding member. In this illustration there is a single prodding element shown, but it is contemplated that multiple prodding elements may be used to engage larger portions of the distal tip of the lumen, aperture of the lumen, wall apertures, and the lumen. This protrusion member 34 is intended to disrupt any obstructions while obstructing suction to a lesser degree than the embodiment of FIG. 5(C).

Figure 5F:
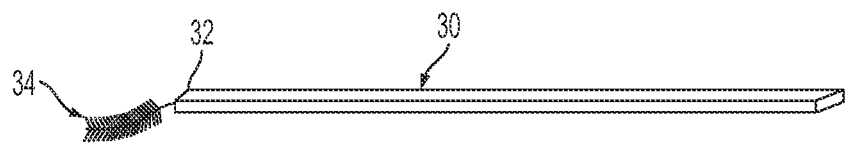

FIG. 5(F) provides a schematic illustration of a perspective view of an embodiment of elongated interacting member 30 of the present invention medical suction device. In this embodiment, the protrusion member 34 consists of a bristled protrusion located at the distal tip 32.

It should be appreciated that changing the contour or size of one or more protrusions will affect the amount of contact area that would be made with the obstructing material and therefore may be adjusted as desired or required for the operation of the device.

The elongated interacting member may also have several protrusion members that are shaped as blunt-tipped teeth that may be used to disrupt any obstructions to the aperture of the lumen, the distal tip of the lumen, or the lumen itself. These blunt tipped teeth may be made to move or pivot as necessary to engage the aperture of the lumen and any wall apertures that are present in the particular embodiment of the device. To achieve this, the blunt-tipped teeth may be formed out of a flexible material that inherently allows their deformation and displacement to engage the aperture of the lumen or any wall apertures. The blunt tipped teeth may also be made of a rigid material and attached to the elongated interacting member with joints, rotating, or pivoting connections to allow them to rotate or articulate into position to engage the aperture of the lumen and any wall apertures that are present.

It is contemplated by the applicant in the context of this invention that there are other viable geometries for the elongated interacting member and protrusion members. The geometry of these parts can vary in size and shape to suit the needs of the users of the device in practice.

Furthermore, it should be appreciated that the elongated interacting member, protrusion members, and the ring-type protrusion member may be manufactured or formed from a multitude of materials that satisfy the working requirements of the invention. This includes, but is not limited to, plastics, polymers, composites, metals, alloys and any combination thereof. This also includes, but is not limited to, materials molded or otherwise formed in order to have changing properties in any fashion including, but not limited to, along their length or across their section. This change in properties may either be by section or continuous in nature. The materials selected for the device 1 may be selected based on ease of manufacturing, price, material properties such as density, strength, modulus of elasticity, electrical or thermal conductivity, and biological compatibility.

Figure 6A:
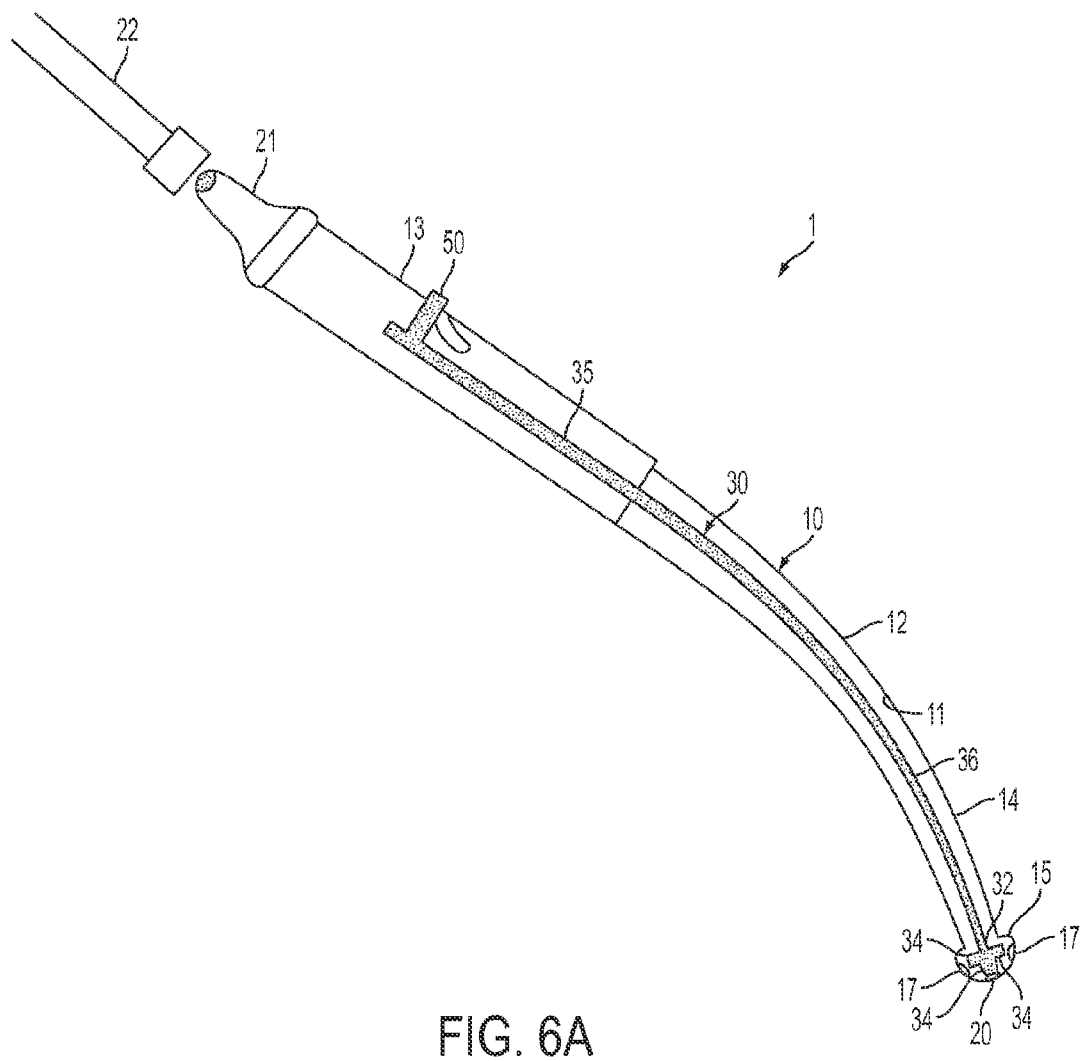
FIG. 6(A) provides a schematic illustration of a perspective view of an embodiment of the present invention medical suction device.

FIG. 6(A) provides a schematic illustration of a perspective view of an embodiment of the present invention medical suction device 1 for use on a subject (not shown) that may be used with a vacuum source (not shown) for the purpose of transferring material from a region of the subject to a collection area. An embodiment of the present invention device 1 may include a lumen 10 having an outer wall 12. The lumen 10 has a distal end 14 and a proximal end 13, and the proximal end 13 may be configured to be in communication (using a port 21, for example) with the vacuum source, such as a hose, tube or connector 22. The distal end 14 may include an aperture 20 at the distal tip 15 of the lumen 10 whereby the lumen 10 is configured to be used in the region of the subject. The device 1 may also include an elongated interacting member 30 that may be substantially aligned with the lumen 10. The elongated interacting member 30 includes a distal end 36 and a proximal end 35. FIG. 6A illustrates the elongated interacting member 30 in a retracted position. The instant illustration of FIG. 6(A) sets forth the elongated interacting member 30 shown in the lumen 10 (below inner wall 11). The device 1 may also include an actuator 50 in communication with the elongated interacting member 30. The actuator 50 is configured to drive the distal end 36 of the elongated interacting member 30. For instance, actuator 50 drives the protrusion members 34 located at the tip 32 of the elongated interacting member 30 through the wall apertures 17 and the lumen aperture 20 to interact with the material to assist the material transfer by mitigating or preventing obstruction of the aperture 20, wall aperture 17, or lumen 10 by the material while the lumen 10 remains in communication with the vacuum source and in the region of the subject.

Figure 6B:
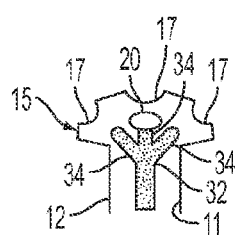
FIG. 6(B) provides an enlarged partial view of the embodiment of the medical suction device of FIG. 6(A) with the elongated interacting member in its retracted position and FIG. 6(C) provides an end view of the device shown in FIG. 6(B).
Figure 6C:
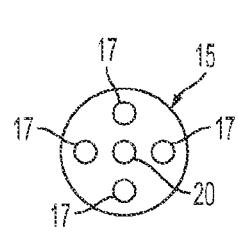
FIG. 6(D) provides an enlarged partial view of the embodiment of the medical suction device of FIG. 6(A) with the elongated interacting member in its deployed position and FIG. 6(E) provides an end view of the device shown in FIG. 6(D).

FIG. 6(B) provides an enlarged partial view of the embodiment of the medical suction device of FIG. 6(A) with the elongated interacting member in its retracted position and FIG. 6(C) provides an end view of the device shown in FIG. 6(B).

Figure 6D:
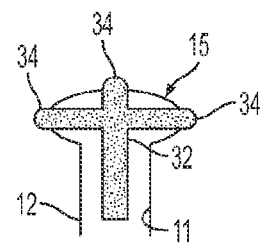
Figure 6E:
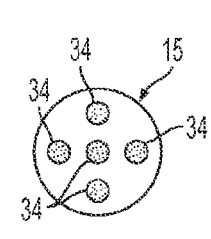

FIG. 6(D) provides an enlarged partial view of the embodiment of the medical suction device of FIG. 6(A) with the elongated interacting member in its deployed position and FIG. 6(E) provides an end view of the device shown in FIG. 6(D).

Figure 7:
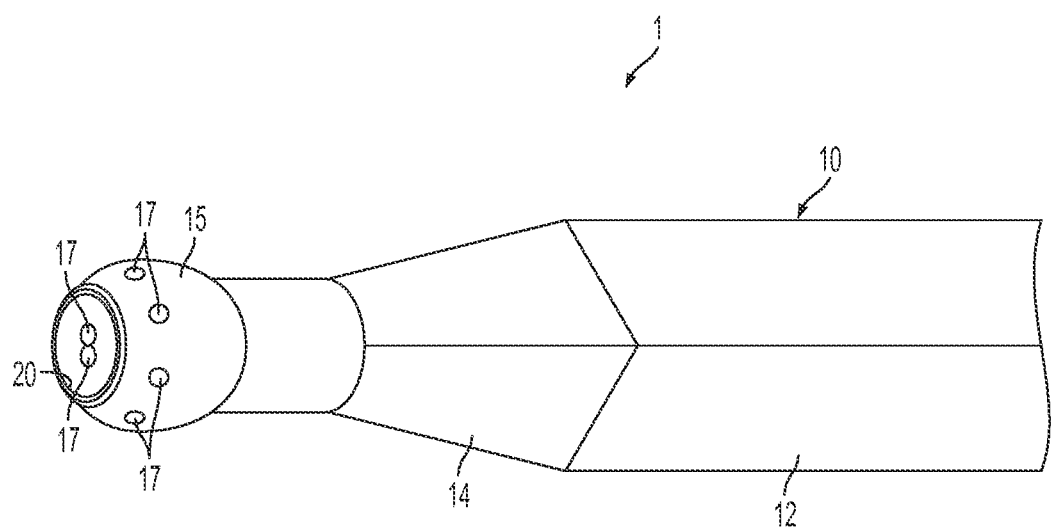
FIG. 7 provides a schematic illustration of a perspective partial view embodiment of the present invention device, including the lumen which a distal end having a lumen aperture at the distal tip of the lumen as well as wall apertures that pass through the wall of the lumen.

FIG. 7 provides a schematic illustration of a perspective partial view embodiment of the present invention device 1 having a lumen 10 and an outer wall 12. The lumen 10 has a distal end 14 having a lumen aperture 20 at the distal tip 15 of the lumen 10 as well as wall apertures 17 that pass through the wall of the lumen 10.

In an approach, an embodiment may include an actuator 50, wherein the elongated interacting member 30 may be displaced by a rack and pinion system. This actuation device would include a toothed rack on the elongated interacting member 30 and an actuator 50, which comprises a rotating wheel coaxial with a toothed pinion gear, mounted so that the rotation axis of the wheel is perpendicular to the centerline of the lumen 10. This actuator 50 would allow the user to roll the rotating wheel to deploy and retract the elongated interacting member 30.

In another approach, an embodiment may include an actuator 50, wherein the elongated interacting member 30 may be displaced by a threaded screw system. This actuator 50 would include a male thread disposed along the length of the elongated interacting member 30 that engages a female thread on the inner surface of a rotating wheel. The rotating wheel would be mounted with its axis of rotation parallel to the centerline of the lumen 10. The user may then roll the rotating wheel to deploy and retract the elongated interacting member 30.

In an approach, an embodiment may include an actuator 50, where the elongated interacting member 30 may be displaced by a sliding mechanism. This actuator 50 would include a grip for the user to slide the elongated interacting member 30 to deploy and retract the elongated interacting member 30.

It should be appreciated that the sliding actuator above could be combined with a guide system comprising grooves or ridges in the inner wall of the lumen 11, the outer wall of the lumen 12, or a retention member 40 that engage the elongated interacting member 30 to guide the elongated interacting member 30 along a particular trajectory. One example would be a helical guide that would twist the elongated interacting member 30 as it is deployed and retracted.

It should be appreciated that the sliding actuator above could be activated by a trigger mechanism.

Another embodiment of the invention would include a mechanism for holding the elongated interacting member 30 stationary or returning it to its retracted position. For instance, the holding mechanism may be a holding member(s) 61 that comprises one or more of the following: a spring, a friction fit member, a gear, a vacuum force (see as generally illustrated in FIGS. 1 and 2).

It should be appreciated that this mechanism could include a spring to return the elongated interacting member 30 to its retracted position.

It should be appreciated that the mechanism for holding the elongated interacting member 30 stationary could include a friction fit between the elongated interacting member 30 and the lumen 10 or a retention member 40. This method could also include holding the elongated interacting member 30 stationary with the friction in a screw type actuator 50.

It should also be appreciated that a mechanism to return the elongated interacting member 30 to its retracted position could include a passage from the vacuum source to the lumen 10 or the elongated hollow chamber 41 to provide suction to retract the elongated interacting member 30.

The applicant also contemplates within the context of this invention that it may be used with a number of different distal lumen tip 15 geometries including, but not limited to, conically shaped, spherically shaped, bulbously shaped, hemisphere-shaped, and cylindrically shaped tips. The tip shape may also include combinations of the above shapes, either together, or with other shapes not mentioned. An example of this would be a conically shaped section in communication with a hemisphere-shaped portion. Different orientations of these geometries are also possible, such as a conically shaped or bulbously shaped tip 15 wherein the longitudinal axis of the tip is parallel to, but offset from, the centerline (CL) of the lumen 10.

Furthermore, the applicant contemplates within the context of this invention that any tip 15 may be separable from the main lumen 10 of the device. These separable tips 15 may be attached through friction, threaded attachment methods, or snap-like attachment methods.

The applicant also contemplates within the context of this invention that any tip may have extra perforations or may include wall apertures 17 in addition to the main lumen aperture 20.

The device 1, any of its components or sub-components, or any portions thereof may be manufactured or formed from a multitude of materials that satisfy the working requirements of the invention. This includes, but is not limited to, plastics, polymers, composites, metals, alloys and any combination thereof. This also includes, but is not limited to, materials molded or otherwise formed in order to have changing properties in any fashion including along their length or across their section. This change in properties may either be sectioned or continuous in nature. The materials selected for the device 1 may be selected based on ease of manufacturing, price, material properties such as density, strength, modulus of elasticity, electrical or thermal conductivity, and biological compatibility.

The applicant contemplates within the context of this invention that it may be produced in any geometrical form with variable length, width, shape, size, or other dimensional variability to match the requirements of specific applications for use.

It should be appreciated that the device 1 may be manufactured in a variety of ways. Specifically, this includes forming, molding, casting, forging, or otherwise producing components, sub-components, or portions thereof. The device may be produced as an assembly of parts wherein those parts are attached in any manner, including but not limited to fusing, welding, friction fits, threaded connections, snap connections, adhesives, or any other method for connecting one component, sub-component, or any portion thereof to another component, sub-component or portion thereof. The device 1 may also be manufactured so as to combine different functional elements into a single, multi-function component that would take on the function of two otherwise separate components.

It is also contemplated that the device 1 may include a handle or grip 23 that is cushioned, enhances grip, tactile feedback, or that is ergonomically shaped for the comfort of the user.

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc.

It should be appreciated that the subject may be any applicable human patient, for example.

An advantage associated with various embodiments of the present invention device ("Gator") includes, but is not limited thereto, that during its use if the tip 15 becomes occluded, the practitioner can clear this occlusion without having to remove the device 1 from the field or use another hand, thus, maintaining visualization and function.

An aspect of various embodiments of the present invention may be utilized for a number of products and services, such as but not limited thereto, the following: providing a device that has wide spread utility in the medical, dental and veterinary fields. It will replace the current suction devices used for procedures in these disciplines. It will be inexpensive, lightweight and disposable.

It should be appreciated that various sizes, dimensions, contours, rigidity, shapes, flexibility and materials of any of the components or portions of components in the various embodiments discussed throughout may be varied and utilized as desired or required. Similarly, locations and alignments of the various components may vary as desired or required.

It should be appreciated that any of the components or modules referred to with regards to any of the present invention embodiments discussed herein, may be integrally or separately formed with one another. Further, redundant functions or structures of the components or modules may be implemented.

It should be appreciated that the device 1 and related components discussed herein may take on all shapes along the entire continual geometric spectrum of manipulation of x, y and z planes to provide and meet the anatomical and structural demands and operational requirements. Moreover, locations and alignments of the various components may vary as desired or required.

EXAMPLES

Practice of an aspect of an embodiment (or embodiments) of the invention will be still more fully understood from the following examples, which are presented herein for illustration only and should not be construed as limiting the invention in any way.

Example Set No. 1

Figure 8A:
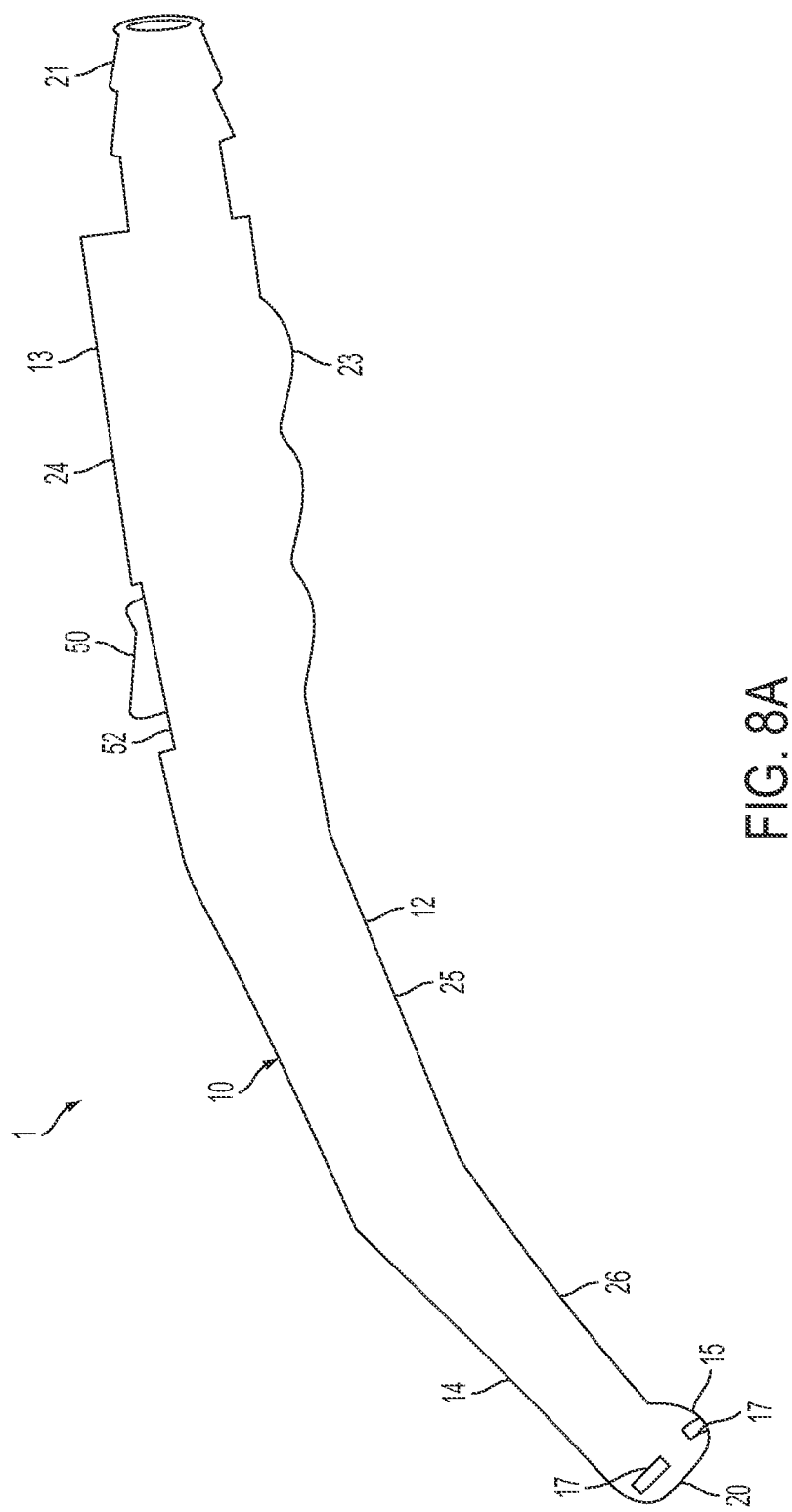
FIG. 8(A) provides a schematic exterior side view of an embodiment of the medical suction device.
Figure 8C:
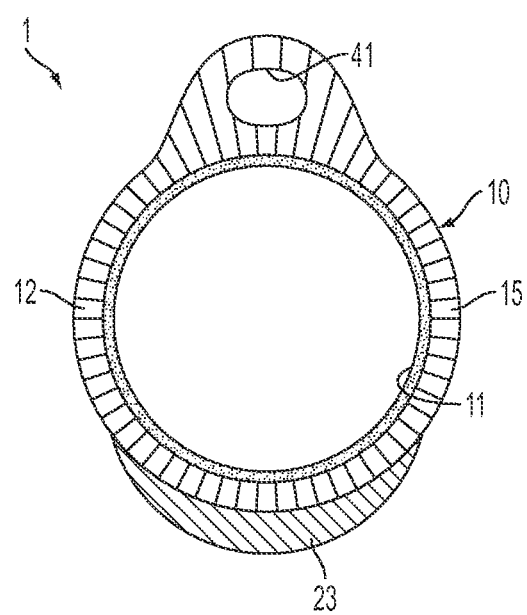
FIG. 8(C) provides an enlarged front sectional view as shown at section 8C-8C, of the embodiment of the medical suction device of FIG. 8(B), but without the elongated interacting member shown.

Turning to FIG. 8, FIG. 8(A) provides a schematic exterior side view of an embodiment of the medical suction device. FIG. 8(B) provides a schematic elevation view of the embodiment of the medical suction device shown in FIG. 8(A). FIG. 8(C) provides an enlarged front section view as shown at section 8C-8C, of the embodiment of the medical suction device of FIG. 8(B), but without the elongated interacting member shown. Referring to FIGS. 8(A)-(C), provided are a schematic illustrations of an embodiment of the present invention medical suction device 1 for use on a subject (not shown) that may be used with a vacuum source (not shown) for the purpose of transferring material from a region of the subject to a collection area. An embodiment of the present invention device 1 may include a lumen 10 having an outer wall 12. The lumen 10 has a distal end 14 and a proximal end 13, and the proximal end 13 may be configured to be in communication (using a port 21, for example) with the vacuum source (not shown). The distal end 14 of the lumen may include an aperture 20 at the distal tip 15 of the lumen 10 whereby the lumen 10 is configured for use in the region of the subject. The device 1 may also include an elongated interacting member 30 that may be substantially aligned with the lumen 10. The elongated interacting member 30 includes a distal end 36 and a proximal end 35. FIG. 8(B) illustrates the elongated interacting member 30 is in a retracted position. The instant illustration of FIG. 8(B) sets forth the elongated interacting member 30 shown in the retention member 40 of lumen 10, in the particular illustration the retention member is an elongated hollow chamber 41. The device 1 may also include an actuator 50 in communication with the elongated interacting member 30. The actuator 50 is configured to drive the distal end 36 of the elongated interacting member 30. For instance, actuator 50 drives the distal tip 32 of the elongated interacting member 30 through the wall apertures 17 and the lumen aperture 20 to interact with the material to assist the material transfer by mitigating or preventing obstruction of the aperture 20 or lumen 10 by the material while the lumen 10 remains in communication with the vacuum source and in the region of the subject. FIGS. 8(A)-(B) also illustrate the first angle segment 24, second angle segment 25, and third angle segment 26 of the lumen 10 and other related components of the device 1. It should be appreciated that the segments may be multitudinous and have unique shapes, sizes, and contours, and the segments may be offset or angled relative to one another as desired or required.

Example Set No. 2

Figure 9:
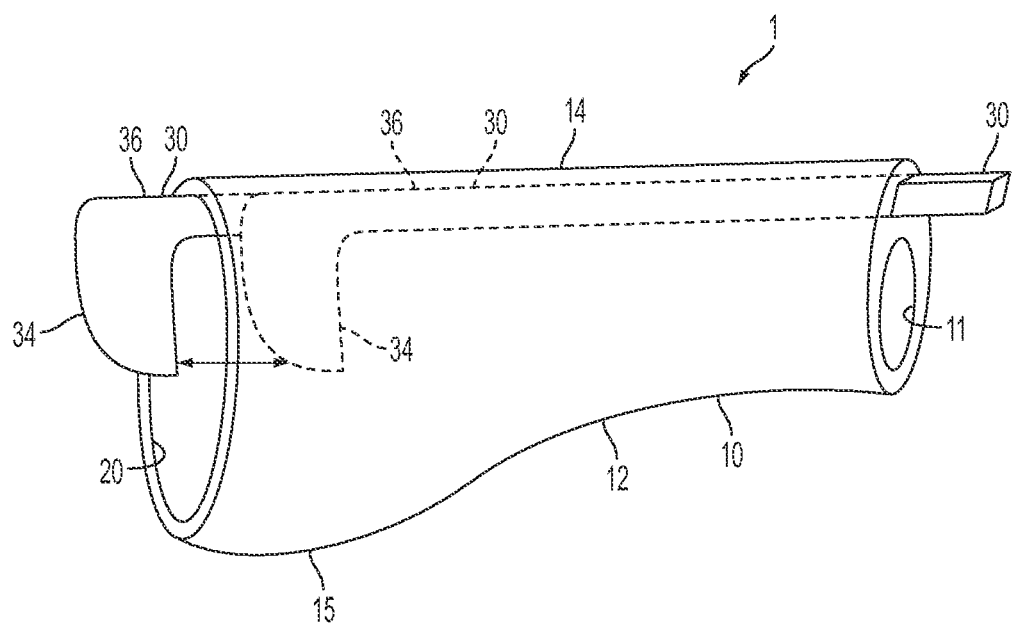
FIG. 9 provides an enlarged partial perspective of an embodiment of the present invention medical suction device, including the distal tip of the lumen.

FIG. 9 provides an enlarged partial perspective of an embodiment of the present invention medical suction device 1 that may include a lumen 10 having an outer wall 12. The lumen 10 has a distal end 14 that may include an aperture 20 at the distal tip 15 of the lumen 10 whereby the lumen 10 is configured to be used in the region of the subject. The device 1 may also include an elongated interacting member 30 that may be substantially aligned with the lumen 10. The elongated interacting member 30 includes a distal end 36 and one or more protrusion members 34. The dashed lines of the interacting member 30 and its distal end 36 illustrate the elongated interacting member 30 in a retracted position. The solid lines of the elongated interacting member 30 and its distal end 36 illustrate the elongated interacting member 30 in a deployed position.

Example Set No. 3

Figure 10:
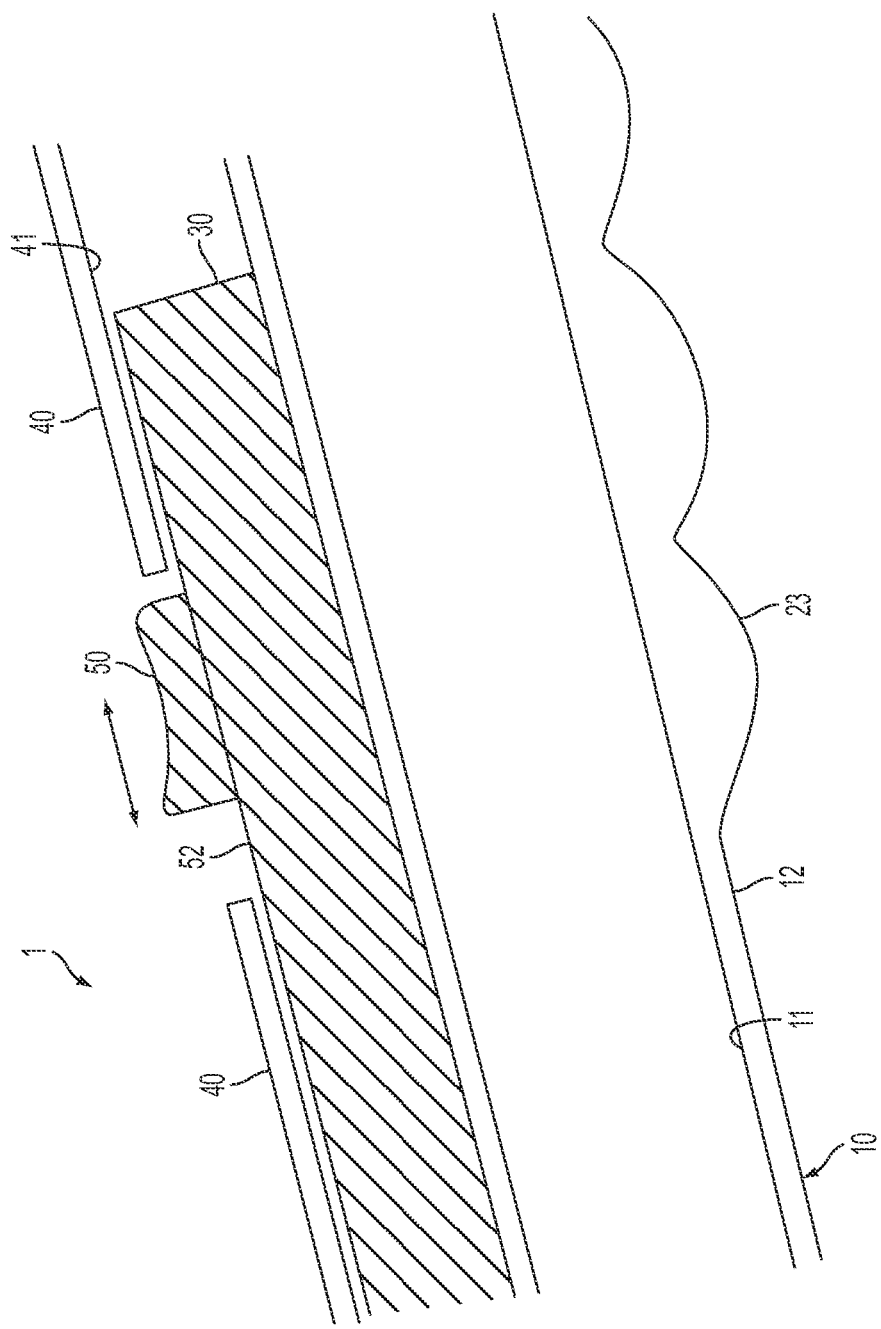
FIG. 10 provides an enlarged partial perspective of an embodiment of the present invention medical suction device, including the actuator.

FIG. 10 provides an enlarged partial perspective of an embodiment of the present invention medical suction device 1 that may include a lumen 10 having an inner wall 11 and outer wall 12. The elongated interacting member 30 is disposed in the retention member 40 being of the type of a hollow chamber 41. The actuator 50 drives the elongated interacting member 30 between various positions, including back and forth. In this example, the gap 52 between the actuator 50 (e.g., thumb piece) and the wall of the hollow chamber 41 dictates the longitudinal distance that the elongated interacting member 30 can travel. Other governors and tolerances for displacement of distance can be implemented as desired or required for the operation of the device 1 and are contemplated as part of the invention.

Example Set No. 4

Figure 11A:
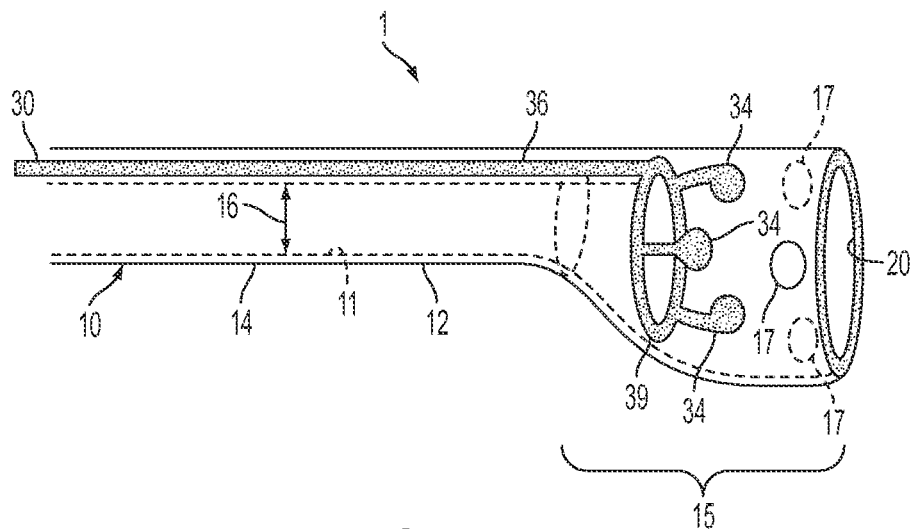
FIG. 11(A) provides an enlarged partial perspective of an embodiment of the present invention medical suction device.
Figure 11B:
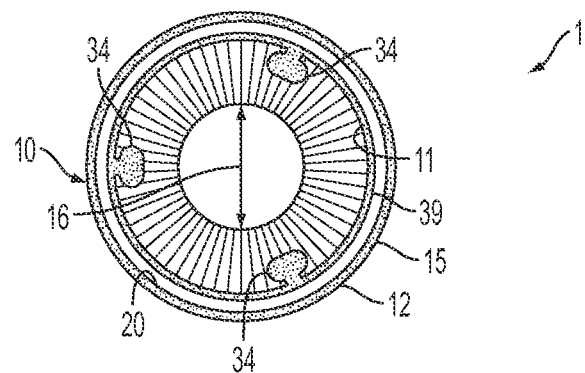
FIG. 11(B) provides an enlarged front view of the embodiment of the medical suction device shown in FIG. 11(A).

FIG. 11(A) provides an enlarged partial perspective of an embodiment of the present invention medical suction device 1 that may include a lumen 10 having an inner wall 11 and outer wall 12. FIG. 11(B) provides an enlarged front view of the embodiment of the medical suction device 1 of FIG. 11(A). Interior diameter 16 of the lumen proximal to the distal tip 15 of the lumen 10 is shown (FIG. 11(A)). The lumen 10 has a distal end 14 that may include an aperture 20 at the distal tip 15 of the lumen 10 whereby the lumen 10 is configured to be used in the region of the subject. The device 1 may also include an elongated interacting member 30 that may be substantially aligned with the lumen 10. The elongated interacting member 30 includes a distal end 36 and one or more protrusion members 34. The actuator (not shown) may be configured to drive the protrusion members 34 located at the tip 32 of the elongated interacting member 30 through or adjacent to the wall apertures 17 and through the lumen aperture 20 to interact with the material to assist the material transfer by mitigating or preventing obstruction of the aperture 20 or lumen 10 by the material while the lumen 10 remains in communication with the vacuum source and in the region of the subject. In the instant embodiment the protrusions are set forth on a portion structured as a ring 39; and it should be appreciated that a variety of geometric shapes or surfaces may be used instead of the ring 39 or in addition to the ring 39 as desired or required.

Additional Examples

Example 1 may include a medical suction device for use on a subject, wherein the device is to be used with a vacuum source for the purpose of transferring material from a region of the subject to a collection area, the device comprising:

a lumen having an inner wall and an outer wall, the lumen having a distal end and a proximal end, the proximal end being in communication with the vacuum source, the distal end including an aperture, wherein the lumen is configured to be used in the region of the subject;

an elongated interacting member substantially aligned with the lumen, the elongated interacting member having a distal end and a proximal end; and an actuator in communication with the elongated interacting member, wherein the actuator is configured to drive the distal end of the elongated interacting member through the aperture or adjacent to the aperture to interact with the material to assist the material transfer by mitigating or preventing obstruction in the aperture or the lumen by the material, while the lumen is configured to remain in communication with the vacuum source and remain in the region of the subject.

Example 2 may optionally include the device of example 1, wherein the driving of the distal end of the elongated interacting member includes the actuator configured to move the elongated interacting member distally to provide the assistance so as to push the material present in the aperture or adjacent to the aperture so as to disrupt the material in the aperture or the lumen.

Example 3 may optionally include the device of example 1 (as well as subject matter of example 2), wherein the driving of the distal end of the elongated interacting member includes the actuator configured to move the elongated member proximally to provide the assistance so as to pull material present in the aperture or adjacent to the aperture so as to disrupt the material in the aperture or the lumen.

Example 4 may optionally include the device of example 3 (as well as subject matter of one or more of any combination of examples 1-2), wherein the driving of the distal end of the elongated interacting member further includes moving the elongated member distally prior to the proximal movement.

Example 5 may optionally include the device of example 1 (as well as subject matter of one or more of any combination of examples 2-4), wherein the distal end of the elongated interacting member comprises a cutting edge, and wherein the driving of the distal end of the elongated interacting member includes the actuator configured to move the elongated interacting member proximally and/or distally to provide the assistance so as to cut the material present in the aperture or adjacent to the aperture so as to disrupt the material in the aperture or the lumen.

Example 6 may optionally include the device of example 5 (as well as subject matter of one or more of any combination of examples 1-4), wherein the cutting edge is proximally facing.

Example 7 may optionally include the device of example 1 (as well as subject matter of one or more of any combination of examples 2-6), wherein the distal end of the elongated interacting member comprises a protrusion, and wherein the driving of the distal end of the elongated interacting member includes the actuator configured to move the elongated interacting member proximally and/or distally to provide the assistance so as to deform the material present in the aperture or adjacent to the aperture so as to disrupt the material in the aperture or the lumen.

Example 8 may optionally include the device of example 1 (as well as subject matter of one or more of any combination of examples 2-7), wherein the elongated interacting member is disposed outside the lumen.

Example 9 may optionally include the device of example 1 (as well as subject matter of one or more of any combination of examples 2-8), wherein the elongated interacting member is disposed inside the lumen.

Example 10 may optionally include the device of example 1 (as well as subject matter of one or more of any combination of examples 2-9), wherein the elongated interacting member is disposed outside the lumen in a retention member that is in communication with the lumen.

Example 11 may optionally include the device of example 10 (as well as subject matter of one or more of any combination of examples 1-9), wherein the retention member comprises an elongated hollow chamber.

Example 12 may optionally include the device of example 10 (as well as subject matter of one or more of any combination of examples 1-9 and/or example 1), wherein the retention member comprises one or more brackets or hooks.

Example 13 may optionally include the device of example 10 (as well as subject matter of one or more of any combination of examples 1-9 and/or examples 11-12), wherein the retention member comprises a combination of an elongated hollow chamber or one or more brackets or hooks.

Example 14 may optionally include the device of example 1 (as well as subject matter of one or more of any combination of examples 2-13), wherein one or more portions of the elongated interacting member are disposed outside the lumen, and one or more portions of the elongated member are disposed inside the lumen.

Example 15 may optionally include the device of example 1 (as well as subject matter of one or more of any combination of examples 2-14), wherein one or more portions of the elongated interacting member are disposed:
within the retention member;
inside the lumen;
outside the lumen; and/or
any combination thereof.

Example 16 may optionally include the device of example 1 (as well as subject matter of one or more of any combination of examples 2-15), wherein the device is hand held wherein the actuator is configured for control by a user during the transferring of the material while the device is in the region of the subject.

Example 17 may optionally include the device of example 1 (as well as subject matter of one or more of any combination of examples 2-16), wherein the distal end of the elongated interacting member comprises one or more protrusions in communication with the distal end of the elongated interacting member.

Example 18 may optionally include the device of example 17 (as well as subject matter of one or more of any combination of examples 1-16), wherein the communication of the one or more protrusions is configured to allow pivoting of the protrusions.

Example 19 may optionally include the device of example 1 (as well as subject matter of one or more of any combination of examples 2-18), wherein the elongated interacting member is made of a flexible material.

Example 20 may optionally include the device of example 1 (as well as subject matter of one or more of any combination of examples 2-19), wherein the elongated interacting member is made of a rigid material.

Example 21 may optionally include the device of example 1 (as well as subject matter of one or more of any combination of examples 2-20), wherein the elongated interacting member is made of a combination of rigid and flexible materials.

Example 22 may optionally include the device of example 1 (as well as subject matter of one or more of any combination of examples 2-21), further comprising a cutting device disposed on the distal end of the elongated interacting member.

Example 23 may optionally include the device of example 22 (as well as subject matter of one or more of any combination of examples 1-21), wherein the cutting device has a cutting surface located on the proximal end of the cutting device.

Example 24 may optionally include the device of example 17 (as well as subject matter of one or more of any combination of examples 1-16 and/or examples 18-23), wherein the one or more protrusions is proximally curved.

Example 25 may optionally include the device of example 17 (as well as subject matter of one or more of any combination of examples 1-16 and/or examples 18-24), wherein the one or more protrusions is rigid or flexible.

Example 26 may optionally include the device of example 17 (as well as subject matter of one or more of any combination of examples 1-16 and/or examples 18-25), wherein the one or more protrusions comprises a brush or bristled protrusion.

Example 27 may optionally include the device of example 17 (as well as subject matter of one or more of any combination of examples 1-16 and/or examples 18-26), wherein the one or more protrusions comprises a hollow member that is configured to allow the material transfer through the aperture or the lumen.

Example 28 may optionally include the device of example 27 (as well as subject matter of one or more of any combination of examples 1-26), wherein the hollow protrusion is a ring.

Example 29 may optionally include the device of example 27 (as well as subject matter of one or more of any combination of examples 1-26 and/or example 28), wherein one or more projections are disposed circumferentially along the perimeter of the hollow protrusion.

Example 30 may optionally include the device of example 17 (as well as subject matter of one or more of any combination of examples 1-16 and/or examples 18-29), wherein the distal end of the lumen has a tip section that includes one or more side apertures traversing through the inner wall and outer wall of the lumen; and wherein the one or more protrusions are disposed in a configuration so as to partially or completely obstruct one or more of the side apertures so as to improve suction through the aperture of the lumen.

Example 31 may optionally include device of example 1 (as well as subject matter of one or more of any combination of examples 2-30), wherein the driving of the distal end of the elongated interacting member includes the actuator configured to displace the elongated interacting member distally and proximally along the lumen.

Example 32 may optionally include the device of example 1 (as well as subject matter of one or more of any combination of examples 2-31), wherein the driving of the distal end of the elongated interacting member includes the actuator configured to slide the elongated interacting member distally and proximally along the lumen.

Example 33 may optionally include the device of example 1 (as well as subject matter of one or more of any combination of examples 2-32), where the actuator comprises a pad or grip to be configured for contact by any digit of the user.

Example 34 may optionally include the device of example 1 (as well as subject matter of one or more of any combination of examples 2-33), where the actuator comprises a contact surface configured for contact by any digit of the user.

Example 35 may optionally include the device of example 1 (as well as subject matter of one or more of any combination of examples 2-34), where the actuator comprises a contact surface configured to be in communication with the user.

Example 36 may optionally include the device of example 1 (as well as subject matter of one or more of any combination of examples 2-35), further comprising a holding member to hold the elongated interacting member stationary and/or retract the elongated interacting member to its proximal position.

Example 37 may optionally include the device of example 36 (as well as subject matter of one or more of any combination of examples 1-35), wherein the holding member comprises one or more of the following: a spring, a friction fit member, a gear, a vacuum force.

Example 38 may optionally include the device of example 1 (as well as subject matter of one or more of any combination of examples 2-37), wherein the lumen is configured with a longitudinal centerline that is substantially straight.

Example 39 may optionally include the device of example 1 (as well as subject matter of one or more of any combination of examples 2-38), wherein the lumen is configured with a longitudinal centerline that is curved.

Example 40 may optionally include the device of example 1 (as well as subject matter of one or more of any combination of examples 2-39), wherein the lumen is configured with a longitudinal centerline, wherein the lumen has multiple segments aligned along the centerline wherein one or more adjacent segments are angled longitudinally or laterally from one another, or any combination thereof.

Example 41 may optionally include the device of example 1 (as well as subject matter of one or more of any combination of examples 2-40), wherein the lumen is configured with a longitudinal centerline, wherein the lumen has curvature along the centerline having a variable radius Example 42 may optionally include the device of example 1 (as well as subject matter of one or more of any combination of examples 2-41), wherein the lumen aperture is cylindrical.

Example 43 may optionally include the device of example 1 (as well as subject matter of one or more of any combination of examples 2-42), wherein the distal end of the lumen has a tip section that is conically shaped.

Example 44 may optionally include the device of example 1 (as well as subject matter of one or more of any combination of examples 2-43), wherein the distal end of the lumen comprises a tip that is bulbously shaped.

Example 45 may optionally include the device of example 44 (as well as subject matter of one or more of any combination of examples 1-43), wherein the bulbous tip has an outside radius larger than the outside radius of the lumen.

Example 46 may optionally include the device of example 1 (as well as subject matter of one or more of any combination of examples 2-45), wherein the distal end of the lumen comprises a tip that is a combination of a conical portion in communication with a hemisphere-shaped portion.

Example 47 may optionally include the device of example 1 (as well as subject matter of one or more of any combination of examples 2-46), wherein the lumen is in communication with a tip disposed on the distal end of the lumen, wherein the tip is detachable and/or attachable.

Example 48 may optionally include the device of example 1 (as well as subject matter of one or more of any combination of examples 2-47), wherein the distal end of the lumen has a tip section that includes one or more side apertures traversing through the inner wall and outer wall of the lumen.

Example 49 may optionally include the device of example 1 (as well as subject matter of one or more of any combination of examples 2-48), further comprising a handle, wherein the handle is in communication with the device.

Example 50 may optionally include the device of example 1 (as well as subject matter of one or more of any combination of examples 2-49), wherein the lumen further comprises a handle.

Example 51 may optionally include the device of example 17 (as well as subject matter of one or more of any combination of examples 1-16 and/or examples 18-50), wherein the driving of the distal end of the elongated interacting member includes the actuator configured to move the elongated interacting member distally to provide the assistance so as to advance the one or more protrusions through the aperture so as to push the material.

Example 52 may optionally include the device of example 17 (as well as subject matter of one or more of any combination of examples 1-16 and/or examples 18-51), wherein the driving of the distal end of the elongated interacting member includes the actuator being configured to move the one or more protrusions proximally through the aperture to provide the assistance so as to pull material through the aperture.

Example 53 may optionally include the device of example 17 (as well as subject matter of one or more of any combination of examples 1-16 and/or examples 18-52), wherein the driving of the distal end of the elongated interacting member includes the actuator configured to move the elongated interacting member distally to provide the assistance so as to advance the one or more protrusions adjacent to the aperture so as to push the material.

Example 54 may optionally include the device of example 17 (as well as subject matter of one or more of any combination of examples 1-16 and/or examples 18-53), wherein the driving of the distal end of the elongated interacting member includes the actuator being configured to move the one or more protrusions proximally adjacent to the aperture to provide the assistance so as to pull material so as to disrupt the material.

Example 55 may optionally include the device of example 17 (as well as subject matter of one or more of any combination of examples 1-16 and/or examples 18-54), wherein the distal end of the lumen has a tip section that includes one or more side apertures traversing through the inner wall and outer wall of the lumen; and wherein the driving of the distal end of the elongated interacting member includes the actuator configured to move the elongated interacting member distally to provide the assistance so as to advance the one or more protrusions through the side aperture so as to push the material.

Example 56 may optionally include the device of example 55 (as well as subject matter of one or more of any combination of examples 1-54), wherein the actuator is also configured to move the elongated interacting member distally to provide the assistance so as to advance the one or more protrusions through the aperture of the lumen so as to push the material.

Side Apertures

Example 57 may optionally include the device of example 17 (as well as subject matter of one or more of any combination of examples 1-16 and/or examples 18-56), wherein the distal end of the lumen has a tip section that includes one or more side apertures traversing through the inner wall and outer wall of the lumen; and wherein the driving of the distal end of the elongated interacting member includes the actuator being configured to move the one or more protrusions proximally through the side apertures to provide the assistance so as to pull material through the side aperture.

Example 58 may optionally include the device of example 57 (as well as subject matter of one or more of any combination of examples 1-56), wherein the actuator is also configured to move the one or more protrusions proximally through the aperture to provide the assistance so as to pull material through the aperture of the lumen.

Example 59 may include a medical suction device (as well as subject matter of one or more of any combination of examples 1-58) for use on a subject for the purpose of transferring material from a region of the subject to a collection area, wherein the device is to be used with a) a lumen having an inner wall and an outer wall, the lumen having a distal end and a proximal end, the proximal end being in communication with the vacuum source, the distal end including an aperture, wherein the lumen is configured to be used in the region of the subject and b) a vacuum source, wherein the device comprises:

an elongated interacting member substantially aligned with the lumen, the elongated interacting member having a distal end and a proximal end; and an actuator in communication with the elongated interacting member, wherein the actuator is configured to drive the distal end of the elongated interacting member through the aperture or adjacent to the aperture to interact with the material to assist the material transfer by mitigating or preventing obstruction in the aperture or the lumen by the material, while the lumen is configured to remain in communication with the vacuum source and remain in the region of the subject.

Example 60 may optionally include the device of example 59 (as well as subject matter of one or more of any combination of examples 1-58), wherein the driving of the distal end of the elongated interacting member includes the actuator configured to move the elongated interacting member distally to provide the assistance so as to push the material present in the aperture or adjacent to the aperture so as to disrupt the material in the aperture or the lumen.

Example 61 may optionally include the device of example 59 (as well as subject matter of one or more of any combination of examples 1-58 and/or example 60), wherein the driving of the distal end of the elongated interacting member includes the actuator configured to move the elongated member proximally to provide the assistance so as to pull material present in the aperture or adjacent to the aperture so as to disrupt the material in the aperture or the lumen.

Example 62 may include a method (which may also include any subject matter of one or more of any combination of examples 1-61) of using medical suction on a subject, wherein the medical suction is provided by a vacuum source, wherein the method is for the purpose of transferring material from a region of the subject to a collection area, the method comprising:

inserting a lumen in the region of the subject;

providing an elongated interacting member substantially aligned with the lumen, the elongated interacting member having a distal end and a proximal end; and driving an actuator in communication with the elongated interacting member to drive the distal end of the elongated interacting member through the lumen or adjacent to lumen to interact with the material to assist the material transfer by mitigating or preventing obstruction in the lumen by the material, as the lumen continues to remain in communication with the vacuum source and remain in the region of the subject.

Example 63 includes the devices, elements, or components discussed in examples 1-62, or any embodiments provided in this disclosure, manufactured using any methods in use, available, or known to a person who is skilled in the art.

The devices, systems, compositions, and methods of various embodiments of the invention disclosed herein may utilize aspects disclosed in the following references, applications, publications and patents and which are hereby incorporated by reference herein in their entirety (and which are not admitted to be prior art with respect to the present invention by inclusion in this section):

1. U.S. Patent Application Publication No. US 2012/0227207A1, Berry, et al., "Medical Suction Clearing Apparatus", Sep. 13, 2002.

2. U.S. Pat. No. 8,262,645 B2, Bagwell, et al., "Devices for Clearing Blockages in In-Situ Artificial Lumens", Sep. 11, 2012.

3. European Patent Specification No. EP 0 906 130 B1, French, et al., "Suction and Irrigation Handpiece and Tip", Jun. 15, 2005.

4. U.S. Pat. No. 8,251,945 B2, Secrest, et al., "Endoscopic Suction Device", Aug. 28, 2012.

5. U.S. Pat. No. 8,298,254 B2, Dubois, et al., "Devices and Methods for Cutting and Evacuating Tissue", Oct. 30, 2012.

6. U.S. Pat. No. 8,292,909 B1, DuBois, et al., "Devices and Methods for Cutting Tissue", Oct. 23, 2012.

7. U.S. Patent Application Publication No. US 2011/0105838 A1, Fogel, R., May 5, 2011.

8. U.S. Pat. No. 7,802,574 B2, Schultz, J., "Medical Component System", Sep. 28, 2010.

9. U.S. Pat. No. 7,244,250 B2, Miki, et al., "Suction Catheter", Jul. 17, 2007.

10. U.S. Pat. No. 7,625,207 B2, Hershey, et al., "Yankauer Suction Device with Sleeve and Wiper", Dec. 1, 2009.

11. U.S. Patent Application Publication No. US 2002/0108614 A1, Schultz, J., "Medical Component System", Aug. 15, 2002.

12. U.S. Patent Application Publication No. US 2005/0279359 A1, LeBlanc, et al., "Oral Suction Catheter", Dec. 22, 2005.

13. U.S. Patent Application Publication No. US 2005/0240165 A1, Miki, et al., "Suction Catheter", Oct. 27, 2005.

14. U.S. Patent Application Publication No. US 2010/0154799 A1, Brewer, et al., "Respiratory Access Assembly with Rotating Lock and Method", Jun. 24, 2010.

15. U.S. Pat. No. 3,469,582, Jackson, R., "Hand-Held Surgical Airflow Instrument", Sep. 30, 1969.

16. U.S. Pat. No. 5,197,949, Angsupanich, K., "Suction Irrigation Device with a Scraper", Mar. 30, 1993.

17. U.S. Pat. No. 5,141,503, Sewell, F., Jr., "Wound Suction Drainage System", Aug. 25, 1992.

18. U.S. Pat. No. 5,269,768, Cheung, V., "Valved Suction Catheter", Dec. 14, 1993.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

We claim:

1. A medical suction device for use on a subject, wherein said device is to be used with a vacuum source for the purpose of transferring material from a region of the subject to a collection area, and for mitigating or preventing obstruction in said device, said device comprising:

a lumen having an inner wall and an outer wall, said lumen having a distal end and a proximal end, said proximal end being in communication with the vacuum source, said distal end including a distal aperture, wherein said lumen is configured to be used in the region of the subject;

a retention member that is in communication with said lumen;

an elongated interacting member substantially aligned with said lumen, said elongated interacting member having a distal end and a proximal end;

an actuator in communication with said elongated interacting member, wherein said actuator is configured to drive said distal end of said elongated interacting member through said distal aperture and adjacent to said distal aperture to interact with the material in said distal aperture or lumen to assist the material transfer by mitigating or preventing obstruction in said distal aperture or said lumen by the material, and wherein said retention member is configured to have said elongated member routed there through, and wherein said retention member is configured to reroute a portion of said elongated member from said retention member through said distal aperture and adjacent to said distal aperture, while said lumen is configured to remain in communication with the vacuum source and remain in the region of the subject; and wherein said distal end of said elongated interacting member that includes:

a ring and a plurality of protrusions that are circumferentially disposed on said distal end ring of said elongated interacting member, and wherein said distal end of said lumen has a tip section that includes:

a plurality of side wall apertures traversing through said inner wall and outer wall of said lumen, wherein said plurality of side wall apertures are circumferentially disposed along said inner wall and outer wall of said lumen and are aligned to coincide with circumferential configuration of said plurality of circumferential protrusions, respectively, whereby the coinciding alignment provides a configuration whereby said plurality of circumferential protrusions obstruct said plurality of side wall apertures so as to improve suction through said distal aperture of said lumen.

2. The device of claim 1, wherein said driving of said distal end of said elongated interacting member includes said actuator configured to move said elongated interacting member distally to provide the assistance so as to push said material present in said distal aperture or adjacent to said distal aperture so as to disrupt the material in said distal aperture or said lumen.

3. The device of claim 2, wherein said driving of said distal end of said elongated interacting member includes said actuator configured to move said elongated member proximally to provide the assistance so as to pull material present in said distal aperture or adjacent to said distal aperture so as to disrupt the material in said distal aperture or said lumen.

4. The device of claim 1, wherein said driving of said distal end of said elongated interacting member includes said actuator configured to move said elongated member proximally to provide the assistance so as to pull material present in said distal aperture or adjacent to said distal aperture so as to disrupt the material in said distal aperture or said lumen.

5. The device of claim 4, wherein said driving of said distal end of said elongated interacting member further includes moving said elongated member distally prior to said proximal movement.

6. The device of claim 1, wherein said distal end of said elongated interacting member comprises a cutting edge, and wherein said driving of said distal end of said elongated interacting member includes said actuator configured to move said elongated interacting member proximally and/or distally to provide the assistance so as to cut the material present in said distal aperture or adjacent to said distal aperture so as to disrupt the material in said distal aperture or said lumen.

7. The device of claim 6, wherein said cutting edge is proximally facing.

8. The device of claim 1, wherein said distal end of said elongated interacting member comprises a distal protrusion, and wherein said driving of said distal end of said elongated interacting member includes said actuator configured to move said elongated interacting member proximally and/or distally to provide the assistance so as to deform the material present in said distal aperture or adjacent to said distal aperture so as to disrupt the material in said distal aperture or said lumen.

9. The device of claim 8, wherein said distal protrusion is proximally curved.

10. The device of claim 8, wherein said distal protrusion is rigid or flexible.

11. The device of claim 8, wherein said distal protrusion comprises a brush or bristled protrusion.

12. The device of claim 8, wherein said driving of said distal end of said elongated interacting member includes said actuator configured to move said elongated interacting member distally to provide the assistance so as to advance said distal protrusion through said distal aperture so as to push said material through said distal aperture.

13. The device of claim 8, wherein said driving of said distal end of said elongated interacting member includes said actuator being configured to move said distal protrusion proximally through said distal aperture to provide the assistance so as to pull material through said distal aperture.

14. The device of claim 8, wherein said driving of said distal end of said elongated interacting member includes said actuator configured to move said elongated interacting member distally to provide the assistance so as to advance said distal protrusion adjacent to said distal aperture so as to push said material.

15. The device of claim 8, wherein said driving of said distal end of said elongated interacting member includes said actuator being configured to move said distal protrusion proximally adjacent to said aperture to provide the assistance so as to pull material so as to disrupt the material.

16. The device of claim 8, wherein said protrusion is configured to allow pivoting of said distal protrusion.

17. The device of claim 1, wherein said elongated interacting member is disposed outside said lumen.

18. The device of claim 1, wherein said elongated interacting member is disposed inside said lumen.

19. The device of claim 1, wherein said retention member is disposed outside said lumen.

20. The device of claim 19, wherein said retention member comprises an elongated hollow chamber.

21. The device of claim 19, wherein said retention member comprises one or more brackets or hooks.

22. The device of claim 19, wherein said retention member comprises:
an elongated hollow chamber and one or more brackets;
an elongated hollow chamber and one or more hooks; or
an elongated hollow chamber and one or more brackets and hooks.

23. The device of claim 1, wherein one or more portions of said elongated interacting member are disposed outside said lumen, and one or more portions of said elongated member are disposed inside said lumen.

24. The device of claim 1, wherein one or more portions of said elongated interacting member are disposed:
within said retention member;
inside said lumen;
outside said lumen; and/or
or any combination thereof.

25. The device of claim 1, wherein said device is hand held wherein said actuator is configured for control by a user during the transferring of said material while the device is in the region of the subject.

26. The device of claim 1, wherein said plurality of said circumferential protrusions are configured to allow pivoting of said plurality of circumferential protrusions.

27. The device of claim 1, wherein said elongated interacting member is made of a flexible material.

28. The device of claim 1, wherein said elongated interacting member is made of a rigid material.

29. The device of claim 1, wherein said elongated interacting member is made of a combination of rigid and flexible materials.

30. The device of claim 1, further comprising a cutting device disposed on the distal end of said elongated interacting member.

31. The device of claim 30, wherein said cutting device has a cutting surface located on the proximal end of said cutting device.

32. The device of claim 1, wherein said driving of said distal end of said elongated interacting member includes said actuator configured to displace said elongated interacting member distally and proximally along said lumen.

33. The device of claim 1, wherein said driving of said distal end of said elongated interacting member includes said actuator configured to slide said elongated interacting member distally and proximally along said lumen.

34. The device of claim 1, where said actuator comprises a pad or grip to be configured for contact by any digit of the user.

35. The device of claim 1, where said actuator comprises a contact surface configured for contact by any digit of the user.

36. The device of claim 1, where said actuator comprises a contact surface configured to be in communication with the user.

37. The device of claim 1, further comprising a holding member to hold said elongated interacting member stationary and/or retract said elongated interacting member to its proximal position.

38. The device of claim 37, wherein said holding member comprises one or more of the following: a spring, a friction fit member, a gear, a vacuum force.

39. The device of claim 1, wherein said lumen is configured with a longitudinal centerline that is substantially straight.

40. The device of claim 1, wherein said lumen is configured with a longitudinal centerline that is curved.

41. The device of claim 1, wherein said lumen is configured with a longitudinal centerline, wherein said lumen has multiple segments aligned along said centerline wherein one or more adjacent segments are angled longitudinally or laterally from one another, or any combination thereof.

42. The device of claim 1, wherein said lumen is configured with a longitudinal centerline, wherein said lumen has curvature along the centerline having a variable radius.

43. The device of claim 1, wherein said lumen is cylindrical.

44. The device of claim 1, wherein said distal end of said lumen has a tip section that is conically shaped.

45. The device of claim 1, wherein said distal end of said lumen comprises a tip that is bulbously shaped.

46. The device of claim 45, wherein said bulbous tip has an outside radius larger than the outside radius of said lumen.

47. The device of claim 1, wherein said distal end of said lumen comprises a tip that is a combination of a conical portion in communication with a hemisphere-shaped portion.

48. The device of claim 1, wherein said lumen is in communication with a tip disposed on the distal end of said lumen, wherein said tip is detachable and/or attachable.

49. The device of claim 1, further comprising a handle, wherein said handle is in communication with said device.

50. The device of claim 1, wherein said lumen further comprises a handle.

51. The device of claim 1, wherein said retention member is disposed inside said lumen.

52. A medical suction device for use on a subject for the purpose of transferring material from a region of the subject to a collection area, and for mitigating or preventing obstruction in said device, wherein said device is to be used with a) a lumen having an inner wall and an outer wall, said lumen having a distal end and a proximal end, said proximal end being in communication with a vacuum source, said distal end including distal aperture, wherein said lumen is configured to be used in the region of the subject, wherein a retention member is in communication with said lumen and b) the vacuum source, wherein said device comprises:
an elongated interacting member substantially aligned with said lumen, said elongated interacting member having a distal end and a proximal end;
an actuator in communication with said elongated interacting member, wherein said actuator is configured to drive said distal end of said elongated interacting member through said distal aperture and adjacent to said distal aperture to interact with the material in said distal aperture or lumen to assist the material transfer by mitigating or preventing obstruction in said distal aperture or said lumen by the material, and wherein said retention member is configured to have said elongated interacting member routed there through, and wherein said retention member is configured to reroute a portion of said elongated interacting member from said retention member through said distal aperture and adjacent to said distal aperture, while said lumen is configured to remain in communication with the vacuum source and remain in the region of the subject; and
wherein said distal end of said elongated interacting member that includes:
a ring and a plurality of protrusions that are circumferentially disposed on said distal end ring of said elongated interacting member, and
wherein said distal end of said lumen has a tip section that includes:
a plurality of side wall apertures traversing through said inner wall and outer wall of said lumen, wherein said plurality of side wall apertures are circumferentially disposed along said inner wall and outer wall of said lumen and are aligned to coincide with circumferential configuration of said plurality of circumferential protrusions, respectively, whereby the coinciding alignment provides a configuration whereby said plurality of circumferential protrusions obstruct said plurality of side wall apertures so as to improve suction through said distal aperture of said lumen.

53. The device of claim 52, wherein said driving of said distal end of said elongated interacting member includes said actuator configured to move said elongated interacting member distally to provide the assistance so as to push said material present in said distal aperture or adjacent to said distal aperture so as to disrupt the material in said distal aperture or said lumen.

54. The device of claim 53, wherein said driving of said distal end of said elongated interacting member includes said actuator configured to move said elongated member proximally to provide the assistance so as to pull material present in said distal aperture or adjacent to said distal aperture so as to disrupt the material in said distal aperture or said lumen.

55. The device of claim 52, wherein said driving of said distal end of said elongated interacting member includes said actuator configured to move said elongated member proximally to provide the assistance so as to pull material present in said distal aperture or adjacent to said distal aperture so as to disrupt the material in said distal aperture or said lumen.

56. The device of claim 55, wherein said driving of said distal end of said elongated interacting member includes said actuator configured to move said elongated interacting member distally to provide the assistance so as to push said material present in said distal aperture or adjacent to said distal aperture so as to disrupt the material in said distal aperture or said lumen.

57. The device of claim 52, wherein said retention member is disposed outside said lumen.

58. The device of claim 52, wherein said retention member is disposed inside said lumen.

* * * * *